US012729384B2

(12) United States Patent
Benenson et al.

(10) Patent No.: US 12,729,384 B2

(45) Date of Patent: Sep. 8, 2026

(54) METHOD TO TREAT DISEASE USING A NUCLEIC ACID VECTOR ENCODING A HIGHLY COMPACT MULTI-INPUT LOGIC GATE

(71) Applicant: Eidgenössische Technische Hochschule Zürich, Zürich (CH)

(72) Inventors: Yaakov Benenson, Binningen (CH); Bartolomeo Angelici, Basel (CH)

(73) Assignee: Eidgenössische Technische Hochschule Zürich, Zürich (CH)

( * ) Notice: Subject to any disclaimer, the term of this patent is extended or adjusted under 35 U.S.C. 154(b) by 853 days.

(21) Appl. No.: 17/283,598

(22) PCT Filed: Oct. 10, 2019

(86) PCT No.: PCT/IB2019/001100

§ 371 (c)(1),
(2) Date: Apr. 8, 2021

(87) PCT Pub. No.: WO2020/074956

PCT Pub. Date: Apr. 16, 2020

(65) Prior Publication Data

US 2021/0381001 A1 Dec. 9, 2021

Related U.S. Application Data

(60) Provisional application No. 62/744,173, filed on Oct. 11, 2018.

(51) Int. Cl.
*C12N 15/63* (2006.01)
*C12N 15/85* (2006.01)
*C12N 15/86* (2006.01)

(52) U.S. Cl.
CPC ............ *C12N 15/85* (2013.01); *C12N 15/86* (2013.01); *C12N 2750/14143* (2013.01); *C12N 2830/40* (2013.01)

(58) Field of Classification Search
CPC .................... C12N 15/85; C12N 15/86; C12N 2750/14143; C12N 2830/40
See application file for complete search history.

(56) References Cited

U.S. PATENT DOCUMENTS

| | | | |
|---|---|---|---|
| 6,287,813 | B1 | 9/2001 | Fussenegger et al. |
| 6,824,994 | B2 | 11/2004 | Weisblum et al. |
| 7,527,942 | B2 | 5/2009 | Carey et al. |
| 7,626,010 | B2 | 12/2009 | Burns et al. |
| 8,105,825 | B2 | 1/2012 | Dhadialla et al. |
| 8,222,221 | B2 | 7/2012 | Corey et al. |
| 9,284,562 | B2 | 3/2016 | Collins et al. |
| 9,458,509 | B2 | 10/2016 | Benenson et al. |
| 10,160,978 | B2 | 12/2018 | Benenson et al. |
| 10,793,921 | B2 | 10/2020 | Benenson et al. |
| 2002/0055172 | A1 | 5/2002 | Harrington |
| 2005/0266561 | A1 | 12/2005 | Wells |
| 2008/0220471 | A1 | 9/2008 | Davis et al. |
| 2009/0192101 | A1 | 7/2009 | Hung et al. |
| 2010/0175141 | A1 | 7/2010 | Collins et al. |
| 2013/0034907 | A1 | 2/2013 | Collins et al. |
| 2013/0202532 | A1 | 8/2013 | Benenson et al. |
| 2017/0145426 | A1 | 5/2017 | Xie et al. |
| 2017/0159135 | A1 | 6/2017 | Benenson et al. |
| 2017/0226530 | A1 | 8/2017 | Benenson et al. |
| 2021/0340526 | A1 | 11/2021 | Mazéet al. |
| 2023/0133209 | A1 | 5/2023 | Benenson et al. |
| 2024/0209357 | A1 | 6/2024 | Benenson et al. |

FOREIGN PATENT DOCUMENTS

| | | | |
|---|---|---|---|
| CN | 101557818 | A | 10/2009 |
| CN | 102716498 | A | 10/2012 |
| CN | 105274059 | A | 1/2016 |
| CN | 106103705 | A | 11/2016 |
| EP | 2684865 | A1 | 1/2014 |
| JP | 2007512027 | A | 5/2007 |
| JP | 2008-545406 | A | 12/2008 |
| JP | 2015503354 | A | 2/2015 |
| JP | 2015063522 | A | 4/2015 |
| WO | WO 2007/000668 | A2 | 1/2007 |
| WO | WO-2007131774 | A1 | 11/2007 |
| WO | WO-2008134593 | A1 | 11/2008 |
| WO | WO-2008157572 | A2 | 12/2008 |
| WO | WO 2012/012739 | A2 | 1/2012 |
| WO | WO 2014/093852 | A1 | 6/2014 |
| WO | WO 2015/188191 | A1 | 12/2015 |
| WO | WO-2015185691 | A1 | 12/2015 |
| WO | WO-2015185692 | A1 | 12/2015 |
| WO | WO-2016095934 | A2 | 6/2016 |

(Continued)

OTHER PUBLICATIONS

Heinz et al., "Graded or threshold response of the tet-controlled gene expression: all depends on the concentration of the transactivator" BMC Biotechnology (2013). 13:5 p. 1-12 (Year: 2013).*
Genoway (https://www.genoway.com/technologies/tet-system) (Year: 2024).*
Hermsen, et al., PLOS Computational Biology (2006) 2(12): 1552-1560 (Year: 2006).*
Geisler and Fechner, World J Exp Med (2016) 6(2): 37-54 (Year: 2016).*
Hasegawa et al., FEBS Letters (2002) 520, 47-52 (Year: 2002).*
Amendola et al., A double-switch vector system positively regulates transgene expression by endogenous microRNA expression (miR-ON vector). Mol Ther. May 2013;21(5):934-46. doi: 10.1038/mt.2013.12. Epub Feb. 26, 2013.

(Continued)

*Primary Examiner* — Evelyn Y Pyla
*Assistant Examiner* — Katherine R Small
(74) *Attorney, Agent, or Firm* — Cooley LLP

(57) ABSTRACT

Disclosed herein are contiguous DNA sequences encoding highly compact multi-input genetic logic gates for precise in vivo cell targeting, and methods of treating disease using a combination of in vivo delivery and such contiguous DNA sequences.

16 Claims, 14 Drawing Sheets

(56) References Cited

FOREIGN PATENT DOCUMENTS

| | | | |
|---|---|---|---|
| WO | WO-2016201106 | A1 | 12/2016 |
| WO | WO 2017/064566 | A2 | 4/2017 |
| WO | WO 2017/132552 | A1 | 8/2017 |
| WO | WO-2018146484 | A1 | 8/2018 |
| WO | WO 2020/074956 | A2 | 4/2020 |
| WO | WO-2020078996 | A1 | 4/2020 |
| WO | WO-2021209813 | A2 | 10/2021 |
| WO | WO-2022117686 | A1 | 6/2022 |

OTHER PUBLICATIONS

Angelici et al., Synthetic Biology Platform for Sensing and Integrating Endogenous Transcriptional Inputs in Mammalian Cells. Cell Rep. Aug. 30, 2016;16(9):2525-37. doi: 10.1016/j.celrep.2016.07.061. Epub Aug. 18, 2016.

Angelici, Design and Implementation of Transcription Factor Based Gene Classifier Circuits. Doctoral Thesis. 2017. doi: 10.3929/ethz-b-000253961. 173 pages.

Ausländer et al., From gene switches to mammalian designer cells: present and future prospects. Trends Biotechnol. Mar. 2013;31(3):155-68. doi: 10.1016/j.tibtech.2012.11.006. Epub Dec. 13, 2012.

Benenson, Biomolecular computing systems: principles, progress and potential. Nat Rev Genet. Jun. 12, 2012;13(7):455-68. doi: 10.1038/nrg3197.

Heinz et al., Graded or threshold response of the tet-controlled gene expression: all depends on the concentration of the transactivator. BMC Biotechnol. Jan. 22, 2013;13:5. doi: 10.1186/1472-6750-13-5. 12 pages.

Szymanski et al., Development and validation of a robust and versatile one-plasmid regulated gene expression system. Mol Ther. Jul. 2007;15(7):1340-7. doi: 10.1038/sj.mt.6300171. Epub May 1, 2007.

Vilaboa et al., Gene switches for deliberate regulation of transgene expression: Recent advances in system development and uses. J Genet Syndr Gene Ther. 2011;2(3):e1000107. doi: 10.4172/2157-7412.1000107. 23 pages.

Al-Zaidy et al., Health outcomes in spinal muscular atrophy type 1 following AVXS-101 gene replacement therapy. Pediatr Pulmonol. Feb. 2019;54(2):179-185. doi: 10.1002/ppul.24203. Epub Dec. 12, 2018.

Ausländer et al., A synthetic multifunctional mammalian pH sensor and CO2 transgene-control device. Mol Cell. Aug. 7, 2014;55(3):397-408 with Supplemental Info. doi: 10.1016/j.molcel.2014.06.007. Epub Jul. 10, 2014. 48 pages.

Ausländer et al., Programmable single-cell mammalian biocomputers. Nature. Jul. 5, 2012;487(7405):123-7. doi: 10.1038/nature11149.

Benenson et al., An autonomous molecular computer for logical control of gene expression. Nature. May 27, 2004;429(6990):423-9. doi: 10.1038/nature02551. Epub Apr. 28, 2004.

Bruce et al., Identification of a motif in the C terminus of herpes simplex virus regulatory protein ICP4 that contributes to activation of transcription. J Virol. Jan. 2002;76(1):195-207. doi: 10.1128/jvi.76.1.195-207.2002.

Choudhury et al., In Vivo Selection Yields AAV-B1 Capsid for Central Nervous System and Muscle Gene Therapy. Mol Ther. Aug. 2016;24(7):1247-57. doi: 10.1038/mt.2016.84. Epub Apr. 27, 2016.

Coulouarn et al., Loss of miR-122 expression in liver cancer correlates with suppression of the hepatic phenotype and gain of metastatic properties. Oncogene. Oct. 8, 2009;28(40):3526-36. doi: 10.1038/onc.2009.211. Epub Jul. 20, 2009.

Dagogo-Jack et al., Tumour heterogeneity and resistance to cancer therapies. Nat Rev Clin Oncol. Feb. 2018;15(2):81-94. doi: 10.1038/nrclinonc.2017.166. Epub Nov. 8, 2017.

Dastor et al., A Workflow for In Vivo Evaluation of Candidate Inputs and Outputs for Cell Classifier Gene Circuits. ACS Synth Biol. Feb. 16, 2018;7(2):474-489. doi: 10.1021/acssynbio.7b00303. Epub Dec. 19, 2017.

Della Peruta et al., Preferential targeting of disseminated liver tumors using a recombinant adeno-associated viral vector. Hum Gene Ther. Feb. 2015;26(2):94-103. doi: 10.1089/hum.2014.052.

Dhungel et al., MicroRNA-Regulated Gene Delivery Systems for Research and Therapeutic Purposes. Molecules. Jun. 21, 2018;23(7):1500. doi: 10.3390/molecules23071500.

Dhungel et al., MicroRNA199a-Based Post-transcriptional Detargeting of Gene Vectors for Hepatocellular Carcinoma. Mol Ther Nucleic Acids. Dec. 7, 2018;13:78-88 and Suppl Info. doi: 10.1016/j.omtn.2018.08.016. Epub Aug. 24, 2018. 13 pages.

Dorer et al., Targeting cancer by transcriptional control in cancer gene therapy and viral oncolysis. Adv Drug Deliv Rev. Jul. 2, 2009;61(7-8):554-71. doi: 10.1016/j.addr.2009.03.013. Epub Apr. 23, 2009.

Duan et al., Consequences of DNA-dependent protein kinase catalytic subunit deficiency on recombinant adeno-associated virus genome circularization and heterodimerization in muscle tissue. J Virol. Apr. 2003;77(8):4751-9. doi: 10.1128/jvi.77.8.4751-4759.2003.

Fussenegger et al., Streptogramin-based gene regulation systems for mammalian cells. Nat Biotechnol. Nov. 2000;18(11):1203-8. doi: 10.1038/81208.

Grimm et al., In vitro and in vivo gene therapy vector evolution via multispecies interbreeding and retargeting of adeno-associated viruses. J Virol. Jun. 2008;82(12):5887-911. doi: 10.1128/JVI.00254-08. Epub Apr. 9, 2008.

Guo et al., Expression features of SOX9 associate with tumor progression and poor prognosis of hepatocellular carcinoma. Diagn Pathol. Apr. 19, 2012;7:44. doi: 10.1186/1746-1596-7-44.

Haefliger et al., Precision multidimensional assay for high-throughput microRNA drug discovery. Nat Commun. Feb. 16, 2016;7:10709. doi: 10.1038/ncomms10709.

Harries et al., Species-specific differences in the expression of the HNF1A, HNF1B and HNF4A genes. PLoS One. Nov. 16, 2009;4(11):e7855. doi: 10.1371/journal.pone.0007855.

Huang et al., Oncolytic adenovirus programmed by synthetic gene circuit for cancer immunotherapy. Nat Commun. Oct. 22, 2019;10(1):4801. doi: 10.1038/s41467-019-12794-2.

Iyer et al., Two-step transcriptional amplification as a method for imaging reporter gene expression using weak promoters. Proc Natl Acad Sci U S A. Dec. 4, 2001;98(25):14595-600. doi: 10.1073/pnas.251551098.

Jüttner et al., Targeting neuronal and glial cell types with synthetic promoter AAVs in mice, non-human primates and humans. Nat Neurosci. Aug. 2019;22(8):1345-1356. doi: 10.1038/s41593-019-0431-2. Epub Jul. 8, 2019.

Kanegae et al., High-level expression by tissue/cancer-specific promoter with strict specificity using a single-adenoviral vector. Nucleic Acids Res. Jan. 2011;39(2):e7. doi: 10.1093/nar/gkq966. Epub Nov. 4, 2010.

Kota et al., Therapeutic microRNA delivery suppresses tumorigenesis in a murine liver cancer model. Cell. Jun. 12, 2009;137(6):1005-17. doi: 10.1016/j.cell.2009.04.021.

Landegger et al., A synthetic AAV vector enables safe and efficient gene transfer to the mammalian inner ear. Nat Biotechnol. Mar. 2017;35(3):280-284. doi: 10.1038/nbt.3781. Epub Feb. 6, 2017.

Liao et al., Identification of SOX4 target genes using phylogenetic footprinting-based prediction from expression microarrays suggests that overexpression of SOX4 potentiates metastasis in hepatocellular carcinoma. Oncogene. Sep. 18, 2008;27(42):5578-89. doi: 10.1038/onc.2008.168. Epub May 26, 2008.

Lillacci et al., Synthetic control systems for high performance gene expression in mammalian cells. Nucleic Acids Res. Oct. 12, 2018;46(18):9855-9863. doi: 10.1093/nar/gky795.

Liu et al., Synthesizing and gate genetic circuits based on CRISPR-Cas9 for identification of bladder cancer cells. Nat Commun. Nov. 6, 2014;5:5393. doi: 10.1038/ncomms6393.

Liu et al., Systematic comparison of 2A peptides for cloning multi-genes in a polycistronic vector. Sci Rep. May 19, 2017;7(1):2193. doi: 10.1038/s41598-017-02460-2.

Morel et al., Cellular heterogeneity mediates inherent sensitivity-specificity tradeoff in cancer targeting by synthetic circuits. Proc

(56) References Cited

OTHER PUBLICATIONS

Natl Acad Sci U S A. Jul. 19, 2016;113(29):8133-8. doi: 10.1073/pnas.1604391113. Epub Jul. 6, 2016.
Navarro et al., Cancer suicide gene therapy: a patent review. Expert Opin Ther Pat. Sep. 2016;26(9):1095-104. doi: 10.1080/13543776.2016.1211640. Epub Jul. 20, 2016.
Nissim et al., A tunable dual-promoter integrator for targeting of cancer cells. Mol Syst Biol. Dec. 21, 2010;6:444. doi: 10.1038/msb.2010.99.
Nissim et al., Synthetic RNA-Based Immunomodulatory Gene Circuits for Cancer Immunotherapy. Cell. Nov. 16, 2017;171(5):1138-1150.e15. doi: 10.1016/j.cell.2017.09.049. Epub Oct. 19, 2017.
Papadakis et al., Promoters and control elements: designing expression cassettes for gene therapy. Curr Gene Ther. Mar. 2004;4(1):89-113. doi: 10.2174/1566523044578077.
Richtig et al., SOX9 is a proliferation and stem cell factor in hepatocellular carcinoma and possess widespread prognostic significance in different cancer types. PLoS One. Nov. 9, 2017;12(11):e0187814. doi: 10.1371/journal.pone.0187814.
Rinaudo et al., A universal RNAi-based logic evaluator that operates in mammalian cells. Nat Biotechnol. Jul. 2007;25(7):795-801. doi: 10.1038/nbt1307. Epub May 21, 2007.
Robson et al., Transcriptional Targeting in Cancer Gene Therapy. J Biomed Biotechnol. 2003;2003(2):110-137. doi: 10.1155/S1110724303209074.
Ruiz et al., MicroRNA-Detargeted Mengovirus for Oncolytic Virotherapy. J Virol. Mar. 28, 2016;90(8):4078-4092. doi: 10.1128/JVI.02810-15.
Sakaguchi et al., Robust cancer-specific gene expression by a novel cassette with hTERT and CMV promoter elements. Oncol Rep. Aug. 2017;38(2):1108-1114. doi: 10.3892/or.2017.5710. Epub Jun. 12, 2017.
Shahbazi et al., Immunostimulants: Types and Functions. J Med Microbiol Infec Dis, 2016;4(3-4):45-51.
Sohn et al., A Single Vector Platform for High-Level Gene Transduction of Central Neurons: Adeno-Associated Virus Vector Equipped with the Tet-Off System. PLoS One. Jan. 6, 2017;12(1):e0169611. doi: 10.1371/journal.pone.0169611. 22 pages.
Uhlen et al., A pathology atlas of the human cancer transcriptome. Science. Aug. 18, 2017;357(6352):eaan2507. doi: 10.1126/science.aan2507.
Weber et al., Emerging biomedical applications of synthetic biology. Nat Rev Genet. Nov. 29, 2011;13(1):21-35. doi: 10.1038/nrg3094.
Xie et al., Multi-input RNAi-based logic circuit for identification of specific cancer cells. Science. Sep. 2, 2011;333(6047):1307-11. doi: 10.1126/science.1205527.
Yang et al., Enzyme-mediated hydrolytic activation of prodrugs. Acta Pharmaceutica Sinica B. 2011;1(3):143-159. doi: 10.1016/j.apsb.2011.08.001.
Ye et al., Self-adjusting synthetic gene circuit for correcting insulin resistance. Nat Biomed Eng. Jan. 2017;1(1):0005. doi: 10.1038/s41551-016-0005. Epub Dec. 19, 2016.
Zhou et al., SOX10 is a novel oncogene in hepatocellular carcinoma through Wnt/ß-catenin/TCF4 cascade. Tumour Biol. Oct. 2014;35(10):9935-40. doi: 10.1007/s13277-014-1893-1. Epub Jul. 8, 2014.
Antunes et al., "Programmable ligand detection system in plants through a synthetic signal transduction pathway". PLoS One. Jan. 25, 2011;6(1): 11 pages.
Atasoy et al., "A FLEX switch targets Channelrhodopsin-2 to multiple cell types for imaging and long-range circuit mapping". Journal of Neuroscience. Jul. 9, 2008;28(28):7025-30.
Ayoubi et al., "Regulation of gene expression by alternative promoters". The FASEB Journal. Mar. 1996;10(4):453-60.
Backman et al., "Use of synchronous site-specific recombination in vivo to regulate gene expression". Bio/Technology. Dec. 1, 1984;2(12):1045-9.
Bashor et al., "Complex signal processing in synthetic gene circuits using cooperative regulatory assemblies". Science. May 10, 2019;364(6440):593-7.
Besant et al., "Mammalian histidine kinases. Biochimica et Biophysica Acta (BBA)-Proteins and Proteomics". Dec. 30, 2005;1754(1-2):281-90.
Böger et al., "Functional determinants for the tetracycline-dependent transactivator tTA in transgenic mouse embryos". Mechanisms of development. May 1, 1999;83(1-2):141-53.
Bindels et al., "mScarlet: a bright monomeric red fluorescent protein for cellular imaging". Nature methods. Jan. 2017; 14(1):53-6.
Bonnet et al., "Amplifying genetic logic gates". Science. May 3, 2013;340(6132):599-603.
Brown et al., "Endogenous microRNA regulation suppresses transgene expression in hematopoietic lineages and enables stable gene transfer". Nature medicine. May 1, 2006;12(5):585-91.
Buchler et al., "On schemes of combinatorial transcription logic". Proceedings of the National Academy of Sciences. Apr. 29, 2003;100(9):5136-41.
Callura et al., "Tracking, tuning, and terminating microbial physiology using synthetic riboregulators". Proceedings of the National Academy of Sciences. Sep. 7, 2010;107(36):15898-903.
Cavicchioli et al., "The NarX and NarQ sensor-transmitter proteins of *Escherichia coli* each require two conserved histidines for nitrate-dependent signal transduction to NarL". Journal of bacteriology. May 1995;177(9):2416-24.
Ceroni et al., "Burden-driven feedback control of gene expression". Nature methods. May 1, 2018;15(5):387-93.
Chen et al: "Cloning, Screening and Sequence Analysis of Bovine Follicle-Stimulating Hormone cDNA". Northwest Agricultural Journal, vol. 1, 1992, with English abstract, 5 pages.
Chen et al., "Synthetic biology: advancing biological frontiers by building synthetic systems". Genome biology. Feb. 2012;13: 10 pages.
Cheung et al., "Structural analysis of ligand stimulation of the histidine kinase NarX". Structure. Feb. 13, 2009;17(2):190-201.
Cho et al., "Universal chimeric antigen receptors for multiplexed and logical control of T cell responses". Cell. May 31, 2018;173(6):1426-38.
Close et al., "Autonomous Bioluminescent Expression of the Bacterial Luciferase Gene Cassette (Lux) in a Mammalian Cell Line", PLoS One, Aug. 27, 2010, 5(8), 12 pages.
Conway et al., "High-titer recombinant adeno-associated virus production utilizing a recombinant herpes simplex virus type I vector expressing AAV-2 Rep and Cap". Gene Therapy. Jun. 1999;6(6):986-93.
Cox et al., "Programming gene expression with combinatorial promoters". Molecular systems biology. Nov. 13, 2007;3(1): 11 pages.
Culler et al., "Reprogramming cellular behavior with RNA controllers responsive to endogenous proteins". Science. Nov. 26, 2010;330(6008):1251-5.
Dale et al., "Gene transfer with subsequent removal of the selection gene from the host genome". Proceedings of the National Academy of Sciences. Dec. 1, 1991;88(23):10558-62.
Deans et al., "A tunable genetic switch based on RNAi and repressor proteins for regulating gene expression in mammalian cells". Cell. Jul. 27, 2007;130(2):363-72.
Donahue et al., "The COMET toolkit for composing customizable genetic programs in mammalian cells". Nature communications. Feb. 7, 2020;11(1): 19 pages.
Doshi et al., "Multiple alternative promoters and alternative splicing enable universal transcription-based logic computation in mammalian cells". Cell Reports. Dec. 1, 2020;33(9), 35 pages.
Dull et al., "A third-generation lentivirus vector with a conditional packaging system" J Virol (1998) 71(11):8463-8471.
Dunlop et al., "Regulatory activity revealed by dynamic correlations in gene expression noise." Nature genetics. Dec. 2008;40(12):1493-8.
Elowitz et al., "A synthetic oscillatory network of transcriptional regulators". Nature. Jan. 20, 2000;403(6767):335-8.

(56) References Cited

OTHER PUBLICATIONS

"Encode" definition; Oxford dictionary; http://www.oxforddictionaries.com/us/definition/american-english/encode; accessed Apr. 27, 2015; 4 pages.
Eperon et al., "Pathways for selection of 5' splice sites by U1 snRNPs and SF2/ASF". The EMBO journal. Sep. 1, 1993;12(9):3607-17.
Eroshenko et al., "Mutants of Cre recombinase with improved accuracy". Nature communications. Sep. 23, 2013;4(1): 10 pages.
Eszterhas et al., "Transcriptional interference by independently regulated genes occurs in any relative arrangement of the genes and is influenced by chromosomal integration position" Molecular and Cellular Biology. 2002. 12 pages.
Filonov et al., "Deep-tissue photoacoustic tomography of a genetically encoded near-infrared fluorescent probe". Angewandte Chemie International Edition. Feb. 6, 2012;51(6):1448-51.
Freeman "The bystander effect: tumor regression when a fraction of the tumor mass is genetically modified". Cancer Res.. 1994;53:1503-6.
Friedland et al., "Synthetic gene networks that count". science. May 29, 2009;324(5931):1199-202.
Gaildrat et al., "Use of splicing reporter minigene assay to evaluate the effect on splicing of unclassified genetic variants". Cancer susceptibility: Methods and protocols. 2010:249-57.
Gam et al., "A mixed antagonistic/synergistic miRNA repression model enables accurate predictions of multi-input miRNA sensor activity". Nature communications. Jun. 22, 2018;9(1):12 pages.
Ganesh et al., "Construction of Methanol-Sensing Escherichia coli by the Introduction of a Paracoccus denitrificans MxaY-Based Chimeric Two-Component System," Journal of microbiology and biotechnology, 2017, vol. 27(6), pp. 1106-1111.
Ganesh et al., "Engineered fumarate sensing *Escherichia coli* based on novel chimeric two-component system," Journal of Biotechnology, 2013, vol. 168(4), pp. 560-566.
Gao et al., "Programmable protein circuits in living cells". Science. Sep. 21, 2018;361(6408):1252-8.
Gardner et al. "Construction of a genetic toggle switch in *Escherichia coli*". Nature. Jan. 20, 2000;403(6767):339-42.
Gibson et al., "Enzymatic assembly of DNA molecules up to several hundred kilobases". Nature methods. May 2009;6(5):343-5.
Gil et al., "Position-dependent sequence elements downstream of AAUAAA are required for efficient rabbit ß-globin mRNA 3' end formation". Cell. May 8, 1987;49(3):399-406.
Glatzel et al., "Adenoviral and adeno-associated viral transfer of genes to the peripheral nervous system". Proceedings of the National Academy of Sciences. Jan. 4, 2000;97(1):442-7.
Greber et al., "Mammalian synthetic biology: engineering of sophisticated gene networks". Journal of biotechnology. Jul. 15, 2007;130(4):329-45.
Green et al., "Complex cellular logic computation using ribocomputing devices". Nature. Aug. 3, 2017;548(7665):117-21.
Grindley et al., "Mechanisms of site-specific recombination". Annu. Rev. Biochem.. Jul. 7, 2006;75(1):567-605.
Ham et al., "Design and construction of a double inversion recombination switch for heritable sequential genetic memory". PLOS One. Jul. 30, 2008;3(7): 9 pages.
Hansen et al., "Transplantation of prokaryotic two-component signaling pathways into mammalian cells". Proceedings of the National Academy of Sciences. Nov. 4, 2014;111(44):15705-10.
Haynes A sensitive switch for visualizing natural gene silencing in single cells. ACS synthetic biology. Mar. 16, 2012;1(3):99-106.
Indra et al., "Temporally-controlled site-specific mutagenesis in the basal layer of the epidermis: comparison of the recombinase activity of the tamoxifen-inducible Cre-ERT and Cre-ERT2 recombinases". Nucleic acids research. Nov. 1, 1999;27(22):4324-7.
International Search Report and Written Opinion for PCT Application No. PCT/EP2015/062507 mailed Aug. 10, 2015, 15 pages.
International Search Report and Written Opinion for PCT Application No. PCT/EP2015/062508 mailed Jul. 23, 2015, 11 pages.
International Search Report and Written Opinion for PCT Application No. PCT/EP2019/077962 mailed Jan. 20, 2020, 12 pages.
International Search Report and Written Opinion for PCT Application No. PCT/EP2021/083846 mailed Feb. 24, 2022, 14 pages.
International Search Report and Written Opinion for PCT Application No. PCT/IB2019/001100 mailed Apr. 1, 2020, 18 pages.
International Search Report and Written Opinion for PCT Application No. PCT/IB2021/000246 mailed Dec. 3, 2021, 32 pages.
International Search Report and Written Opinion for PCT Application No. PCT/US2011/045038 mailed Mar. 28, 2012, 17 pages.
Invitation to Pay Additional Fees for International Application No. PCT/IB2019/001100, mailed Feb. 11, 2020, 16 pages.
Invitation to Pay Additional Fees for International Application No. PCT/IB2021/000246, mailed Oct. 12, 2021, 24 pages.
June et al., "CAR T cell immunotherapy for human cancer". Science. Mar. 23, 2018;359(6382):1361-5.
Kanno et al., "Intein-Mediated Reporter Gene Assay for Detecting Protein-Protein Interactions in Living Mammalian Cells". Analytical chemistry. Jan. 15, 2006;78(2):556-60.
Keeler et al., "Recombinant adeno-associated virus gene therapy in light of Luxturna (and Zolgensma and Glybera): where are we, and how did we get here?". Annual review of virology. Sep. 29, 2019;6(1):601-21.
Kloss et al., "Combinatorial antigen recognition with balanced signaling promotes selective tumor eradication by engineered T cells". Nature biotechnology. Jan. 2013;31(1):71-5.
Kozak "Point mutations define a sequence flanking the AUG initiator codon that modulates translation by eukaryotic ribosomes," Cell. Jan. 31, 1986; 44(2):283-92.
Kramer et al., "BioLogic gates enable logical transcription control in mammalian cells". Biotechnology and bioengineering. Aug. 20, 2004;87(4):478-84.
Kubokawa et al., "Molecular characterization of the 5'-UTR of retinal dystrophin reveals a cryptic intron that regulates translational activity". Molecular vision. Dec. 7, 2010;16: 8 pages.
Lapique et al., "Digital switching in a biosensor circuit via programmable timing of gene availability". Nature chemical biology. Dec. 2014;10(12):1020-7.
Lapique et al., "Genetic programs can be compressed and autonomously decompressed in live cells". Nature nanotechnology. Apr. 2018;13(4):309-15.
Leisner et al., "Rationally designed logic integration of regulatory signals in mammalian cells". Nature nanotechnology. Sep. 2010;5(9):666-70.
Li et al., "Deletions of the Aequorea victoria green fluorescent protein define the minimal domain required for fluorescence". Journal of Biological Chemistry. Nov. 7, 1997;272(45):28545-9.
Lin et al., "How different eukaryotic transcriptional activators can cooperate promiscuously". Nature. May 24, 1990;345(6273):359-61.
Llovet et al., "mRECIST for HCC: performance and novel refinements". Journal of hepatology. Feb. 1, 2020;72(2):288-306.
Lloyd et al., "Modelling the human immune response: performance of a 1011 human antibody repertoire against a broad panel of therapeutically relevant antigens". Protein Engineering, Design & Selection. Mar. 1, 2009;22(3):159-68.
Lohmueller et al., "A tunable zinc finger-based framework for Boolean logic computation in mammalian cells". Nucleic acids research. Jun. 1, 2012;40(11):5180-7.
Lois et al., Germline transmission and tissue-specific expression of transgenes delivered by lentiviral vectors'. science. Feb. 1, 2002;295(5556):868-72.
Lytle et al., "Target mRNAs are repressed as efficiently by microRNA-binding sites in the 5' UTR as in the 3' UTR". Proceedings of the National Academy of Sciences. Jun. 5, 2007;104(23):9667-72.
Mansfield et al., "MicroRNA-responsive 'sensor' transgenes uncover Hox-like and other developmentally regulated patterns of vertebrate microRNA expression," Nature genetics. Oct. 1, 2004;36(10):1079-83.
Mathur et al., "Programmable mutually exclusive alternative splicing for generating RNA and protein diversity". Nature communications. Jun. 17, 2019;10(1): 13 pages.

(56) References Cited

OTHER PUBLICATIONS

Maze et al., "Artificial signaling in mammalian cells enabled by prokaryotic two-component system". Nature chemical biology. Feb. 2020;16(2):179-87.
Misirly et al. "A computational workflow for the automated generation of models of genetic designs". ACS synthetic biology. May 21, 2018;8(7):1548-59.
Miyaso et al., "An intronic splicing enhancer element in survival motor neuron (SMN) pre-mRNA". Journal of Biological Chemistry. May 2, 2003;278(18):15825-31.
Mohammadi et al., "Automated design of synthetic cell classifier circuits using a two-step optimization strategy". Cell systems. Feb. 22, 2017;4(2):207-18.
Muhlethaler-Mottet et al, ."Expression of MHC class II molecules in different cellular and functional compartments is controlled by differential usage of multiple promoters of the transactivator CIITA." The EMBO journal. May 15, 1997. 10 pages.
Mukherji et al., "Synthetic biology: understanding biological design from synthetic circuits". Nature Reviews Genetics. Dec. 2009;10(12):859-71.
Nelson et al., "In vivo genome editing improves muscle function in a mouse model of Duchenne muscular dystrophy". Science. Jan. 22, 2016;351(6271):403-7.
Nickerson et al., "Dendritic cell-specific MHC class II transactivator contains a caspase recruitment domain that confers potent transactivation activity". Journal of Biological Chemistry. Jun. 1, 2001;276(22):19089-93.
Nielsen et al., "Advances in genetic circuit design: novel biochemistries, deep part mining, and precision gene expression". Current opinion in chemical biology. Dec. 1, 2013;17(6):878-92.
Nielsen et al., "Genetic circuit design automation". Science. Apr. 1, 2016;352(6281):10 pages.
Paterna et al., "Transduction profiles of recombinant adeno-associated virus vectors derived from serotypes 2 and 5 in the nigrostriatal system of rats". Journal of virology. Jul. 1, 2004;78(13):6808-17.
Piovesan et al., "Identification of minimal eukaryotic introns through GeneBase, a user-friendly tool for parsing the NCBI Gene databank". DNA Research. Dec. 1, 2015;22(6):495-503.
Poling et al., "A lentiviral vector bearing a reverse intron demonstrates superior expression of both proteins and microRNAs". RNA biology. Nov. 2, 2017;14(11):1570-9.
Prochazka et al., "Highly modular bow-tie gene circuits with programmable dynamic behaviour". Nature communications. Oct. 14, 2014;5(1): 12 pages.
Rickman et al., "A two-component signal transduction system with a PAS domain-containing sensor is required for virulence of Mycobacterium tuberculosis in mice". Biochemical and biophysical research communications. Jan. 30, 2004;314(1):259-67.
Rizzo et al., "High-contrast imaging of fluorescent protein FRET by fluorescence polarization microscopy". Biophysical journal. Feb. 1, 2005;88(2); 3 pages.
Rosenberg et al., "Learning the sequence determinants of alternative splicing from millions of random sequences". Cell. Oct. 22, 2015;163(3):698-711.
Roybal et al., "Engineering T cells with customized therapeutic response programs using synthetic notch receptors". Cell. Oct. 6, 2016;167(2):419-32.
Sasaki-Haraguchi et al., "Mechanistic insights into human pre-mRNA splicing of human ultra-short introns: potential unusual mechanism identifies G-rich introns". Biochemical and biophysical research communications. Jun. 29, 2012;423(2):289-94.
Schnutgen et al., "A directional strategy for monitoring Cre-mediated recombination at the cellular level in the mouse," Nature Biotechnology, 2003, vol. 21, pp. 562-565.
Scholl et al., "Emerging therapies for inherited retinal degeneration". Science translational medicine. Dec. 7, 2016;8(368):10 pages.
Schramm et al., "InSiDDe: A server for designing artificial disordered proteins". International journal of molecular sciences. Dec. 29, 2017;19(1): 15 pages.
Schreiber et al., "Model-guided combinatorial optimization of complex synthetic gene networks". Molecular Systems Biology. Dec. 2016;12(12): 14 pages.
Sektas et al., "Expression plasmid with a very tight two-step control: Int/att-mediated gene inversion with respect to the stationary promoter". Gene. Apr. 18, 2001;267(2):213-20.
Sektas et al., "Tightly controlled two-stage expression vectors employing the Flp/FRT-mediated inversion of cloned genes". Molecular biotechnology. Feb. 1998;9:17-24.
Shcherbakova et al., "Bright monomeric near-infrared fluorescent proteins as tags and biosensors for multiscale imaging". Nature communications. Aug. 19, 2016;7(1):12 pages.
Siegert et al., "Transcriptional code and disease map for adult retinal cell types". Nature neuroscience. Mar. 2012;15(3):487-95.
Siuti et al., "Synthetic circuits integrating logic and memory in living cells". Nature biotechnology. May 2013;31(5):448-52.
Stanton et al., "Systematic transfer of prokaryotic sensors and circuits to mammalian cells". ACS synthetic biology. Dec. 19, 2014;3(12):880-91.
Tamsir et al., "Robust multicellular computing using genetically encoded NOR gates and chemical 'wires'". Nature. Jan. 13, 2011;469(7329):212-5.
Tastanova et al., "Synthetic biology-based cellular biomedical tattoo for detection of hypercalcemia associated with cancer. Science translational medicine". Apr. 18, 2018;10(437), 11 pages.
Uphoff et al., "Detecting mycoplasma contamination in cell cultures by polymerase chain reaction". Cancer cell culture: methods and protocols. 2011:93-103.
Wang et al., "Intronic splicing enhancers, cognate splicing factors and context-dependent regulation rules". Nature structural & molecular biology. Oct. 2012;19(10):1044-52.
Weber et al., "A synthetic mammalian gene circuit reveals antituberculosis compounds". Proceedings of the National Academy of Sciences. Jul. 22, 2008;105(29):9994-8.
Weber et al., "Engineering of synthetic mammalian gene networks." Chemistry & biology. Mar. 27, 2009;16(3):287-97.
Weber et al., "Macrolide-based transgene control in mammalian cells and mice". Nat Biotechnol. Sep. 2002;20(9):901-7.
Weinberg et al., "Large-scale design of robust genetic circuits with multiple inputs and outputs for mammalian cells". Nature biotechnology. May 2017;35(5):453-62.
Xie et al., "Designing cell function: assembly of synthetic gene circuits for cell biology applications". Nature Reviews Molecular Cell Biology. Aug. 2018; 19(8):507-25.
Yeo et al., "Maximum entropy modeling of short sequence motifs with applications to RNA splicing signals". InProceedings of the seventh annual international conference on Research in computational molecular biology Apr. 10, 2003 pp. 322-331.
You et al., "Programmed population control by cell-cell communication and regulated killing". Nature. Apr. 22, 2004;428(6985):868-71.
Zah et al., "T cells expressing CD19/CD20 bispecific chimeric antigen receptors prevent antigen escape by malignant B cells". Cancer immunology research. Jun. 1, 2016;4(6):498-508.
Zhang et al., "Design of a dynamic sensor-regulator system for production of chemicals and fuels derived from fatty acids". Nature biotechnology. Apr. 2012;30(4):354-9.
Zhang et al., "Efficient construction of sequence-specific TAL effectors for modulating mammalian transcription" Nature Biotechnology (2011); 29(2):149-153.
Gonzalez-Nicolini et al., "A novel binary adenovirus-based dual-regulated expression system for independent transcription control of two different transgenes". The Journal of Gene Medicine: A cross-disciplinary journal for research on the science of gene transfer and its clinical applications. Dec. 2005; 7(12):1573-85.
Milbrandt et al., "Structure of the VP16 transactivator target in the Mediator". Nature structural & molecular biology. Apr. 2011;18(4):410-5.
Roney et al., "Improvement of the reverse tetracycline transactivator by single amino acid substitutions that reduce leaky target gene expression to undetectable levels". Scientific reports. Jun. 21, 2016;6(1): 8 pages.

(56) References Cited

OTHER PUBLICATIONS

Matsuura et al., "Synthetic RNA-based logic computation in mammalian cells". Nature communications. Nov. 19, 2018;9(1):8 pages.

* cited by examiner

Circuit Performance in Lentiviral
Vectors: On:Off is preserved
A None
B A1 A3
C F1 C3
Fluorescence Intensity
$10^5$
$10^4$
$10^3$
$10^2$
10
1
HUH7
HepG2
HCT-116
A
B
C A1 A3 Insulated Circuit:
Expression Over Time
A HepG2
B Huh7
C HCT-116
Fluorescence Intensity
$10^6$
$10^5$
$10^4$
$10^3$
$10^2$
10
1
0.1
Time (Days)
0
10
20
30
40
50
60

FIG. 6A
ITR
PolyA
PIT-VP16
TATA
Spy RE
PIT RE
Hnf1 RE
TATA
mCherry
PolyA
T-miR-122
ITR
I.V injection
Wait for disseminated tumor establishment
Liver
Spleen
HEPG2-LC

Circuit program
Constitutive mCherry
HNF1A/B AND SOX9/10
HNF1A/B AND SOX9/10 AND NOT(miR-122)

Liver Section

HepG2 Tumor (Yellow)

Circuit output expression (mCherry)

Number of Inputs processed by the circuit
0
2
3

DNA schematics
Option 1
Option 1+3a

T-miR-122
ITR
PolyA
PIT-VP16
TATA
Sox RE
PIT RE
Hnf1 RE
TATA
HSV-TK
PolyA
ITR

IV injection d15
IV injection d22
Spleen
Liver
d18
HEPG2-LC
daily I.P GCV 50 mg/kg
or Saline

METHOD TO TREAT DISEASE USING A NUCLEIC ACID VECTOR ENCODING A HIGHLY COMPACT MULTI-INPUT LOGIC GATE

RELATED APPLICATIONS

This Application is a national stage filing under 35 U.S.C. 371 of International Patent Application Serial No. PCT/IB2019/001100, filed Oct. 10, 2019, which claims the benefit under 35 U.S.C. 119(e) of U.S. Provisional Application Ser. No. 62/744,173, filed Oct. 11, 2018, the content of each of which is incorporated by reference herein in its entirety.

FIELD

Disclosed herein are contiguous DNA sequences encoding highly compact multi-input genetic logic gates for precise in vivo cell targeting, and methods of treating disease using a combination of in vivo delivery and such contiguous DNA sequences.

BACKGROUND

Gene therapy is on the rise as a next generation therapeutic option for genetic disease and cancer. However, current gene therapy vectors are plagued by low efficacy, high toxicity, and long developmental timelines to generate therapeutic leads. One reason for these drawbacks is insufficiently tight control of therapeutic gene expression in the gene therapy vector which leads to gene expression (i) in unintended cell types and tissues or (ii) at either insufficient or too-high dosage. In other words, precise control of gene expression, both in terms of gene product dosage (i.e., the number of protein molecules per cell) and cell type-restricted expression remains an open challenge in gene therapy.

SUMMARY

Engineering contiguous DNA molecules that contain multiple components required for multi-feature cell probing and generating an appropriate therapeutic action is a very challenging task even when the initial building blocks are partially known. This disclosure describes an approach to engineer contiguous DNA molecules that encode a complex multi-input genetic logic circuit capable of probing multiple transcription factors and/or promoter activities, and optionally, microRNA features, simultaneously. As such, the contiguous molecule is suitable for implementation in a wide variety of viral vectors, including vectors with low packaging capacity but high therapeutic value (e.g., AAV, Lentivirus, Adenovirus), non-replicating and replicating viruses, as well as non-viral delivery vectors. The resulting viruses and non-viral delivery vectors can be used to selectively target specific cell types or cell states both in vivo and in vitro and used as therapies.

In some aspects, the disclosure relates to contiguous polynucleic acid molecules encoding at least two cassettes, wherein each cassette comprises a regulatory component and a response component.

In some embodiments: (i) at least one cassette comprises: a 5' regulatory component comprising a transactivator response element and a 3' response component comprising an output; and (ii) at least one cassette comprises: a 5' regulatory component and a 3' response component comprising a nucleic acid sequence encoding a transactivator protein; and wherein the transactivator of (ii), when expressed as a protein, binds and transactivates the transactivator response element of (i).

In some embodiments, the transactivator binds and transactivates the transactivator response element independently.

In some embodiments, the 5' regulatory component of the cassette in (i) further comprises a transcription factor response element and/or a minimal promoter. In other embodiments, the transactivator binds and transactivates the transactivator response element only in the presence of a transcription factor bound to the transcription factor response element.

In some embodiments, the 5' regulatory component comprises from 5' to 3': the transactivator response element, the transcription factor response element, and the minimal promoter. In some embodiments, the 5' regulatory component comprises from 5' to 3': the transcription factor response element, the transactivator response element, and the minimal promoter.

In some embodiments, the 5' regulatory component in (i) further comprises a promoter element. In some embodiments, the promoter element comprises a mammalian promoter or promoter fragment.

In some embodiments, the 5' regulatory component comprises from 5' to 3': the transactivator response component and a promoter element and, optionally, a minimal promoter.

In some embodiments, the 5' regulatory component of the cassette in (ii) comprises a promoter element. In some embodiments, the promoter element comprises a transcription factor response element and a minimal promoter, optionally wherein the transcription factor response element is unique. In some embodiments, the promoter element comprises a mammalian promoter or promoter fragment and, optionally, a minimal promoter.

In some embodiments, at least one cassette of (i) and at least one cassette of (ii) are in a convergent orientation. In some embodiments, at least one cassette of (i) and at least one cassette of (ii) are in a divergent orientation. In some embodiments, at least one cassette of (i) and at least one cassette of (ii) are in a head-to-tail orientation.

In some embodiments, the 3' response component of the cassette in (i) further comprises at least one microRNA target site. In some embodiments, at least one microRNA target site is 3' to the output. In some embodiments, at least one microRNA target site is 5' to the output or within the output.

In some embodiments, the cassette in (ii) further comprises at least one microRNA target site. In some embodiments, the at least one microRNA target site is 3' to the transactivator protein-coding DNA sequence. In some embodiments, the at least one microRNA target site is 5' to the transactivator protein-coding DNA sequence or within the the transactivator protein-coding DNA sequence.

In some embodiments, the at least one microRNA target site of the cassette in (i) and at least one microRNA target site of the cassette in (ii) are the same nucleic acid sequence or are different sequences regulated by the same microRNA.

In some embodiments, at least one cassette is flanked by an insulator.

In some embodiments, the transactivator of at least one cassette is tTA, rtTA, PIT-RelA, PIT-VP16, ET-VP16, ET-RelA, NarLc-VP16, or NarLc-RelA.

In some embodiments, the output is a protein or an RNA molecule. In some embodiments, the output is a therapeutic. In some embodiments, the output is a fluorescent protein, a cytotoxin, an enzyme catalyzing a prodrug activation, an immunomodulatory protein and/or RNA, a DNA-modifying factor, cell-surface receptor, a gene expression-regulating factor, a kinase, an epigenetic modifier, and/or a factor necessary for vector replication. In some embodiments, the immunomodulatory protein and/or RNA is a cytokine or a colony stimulating factor. In some embodiments, the DNA-modifying factor is a gene encoding a protein intended to correct a genetic defect, a DNA-modifying enzyme, and/or a component of a DNA-modifying system. In some embodiments, the DNA-modifying enzyme is a site-specific recombinase, homing endonuclease, or a protein component of a CRISPR/Cas DNA modification system. In some embodiments, the gene expression-regulating factor is a protein capable of regulating gene expression or a component of a multi-component system capable of regulating gene expression.

In some aspects, the disclosure relates to contiguous polynucleic acid molecules encoding at least one cassette, wherein the cassette comprises: (i) a 5' regulatory component comprising a transactivator response element; and (ii) a 3' response component comprising an output, a transactivator, and an optional polycistronic expression element, wherein the output and the transactivator are optionally separated by the polycistronic expression element; wherein transcription of the response component generates a single mRNA; and wherein the transactivator of (ii), when expressed as a protein, binds and transactivates the transactivator response element of (i).

In some embodiments, the transactivator binds and transactivates the transactivator response element independently.

In some embodiments, the 5' regulatory component in (i) further comprises a transcription factor response element and/or a minimal promoter. In some embodiments, the transactivator binds and transactivates the transactivator response element only in the presence of a transcription factor bound to the transcription factor response element.

In some embodiments, the 5' regulatory component comprises from 5' to 3': the transactivator response element, the transcription factor response element, and the minimal promoter. In some embodiments, the 5' regulatory component comprises from 5' to 3': the transcription factor response element, the transactivator response element, and the minimal promoter.

In some embodiments, the 5' regulatory component in (i) further comprises a promoter element. In some embodiments, the promoter element comprises a mammalian promoter or promoter fragment. In some embodiments, the 5' regulatory component in (i) comprises from 5' to 3': a transactivator response component and a promoter element.

In some embodiments, the 3' response component of (ii) further comprises at least one microRNA target site. In some embodiments, the at least one microRNA target site is 3' to the output and/or transactivator. In some embodiments, the at least one microRNA target site is 5' to the output and/or transactivator or inside the output and/or transactivator.

In some embodiments, at least one cassette is flanked by an insulator.

In some embodiments, the transactivator of at least one cassette is tTA, rtTA, PIT-RelA, PIT-VP16, ET-VP16, ET-RelA, NarLc-VP16, or NarLc-RelA.

In some embodiments, the output is a protein or an RNA molecule. In some embodiments, the output is a therapeutic protein or RNA molecule. In some embodiments, the output is a fluorescent protein, a cytotoxin, an enzyme catalyzing a prodrug activation, an immunomodulatory protein and/or RNA, a DNA-modifying factor, cell-surface receptor, a gene expression-regulating factor, a kinase, an epigenetic modifier, and/or a factor necessary for vector replication. In some embodiments, the immunomodulatory protein and/or RNA is a cytokine or a colony stimulating factor. In some embodiments, the DNA-modifying factor is a gene encoding a protein intended to correct a genetic defect, a DNA-modifying enzyme, and/or a component of a DNA-modifying system. In some embodiments, the DNA-modifying enzyme is a site-specific recombinase, homing endonuclease, or a protein component of a CRISPR/Cas DNA modification system. In some embodiments, the gene expression-regulating factor is a protein capable of regulating gene expression or a component of a multi-component system capable of regulating gene expression.

In some aspects, the disclosure relates to vectors comprising a contiguous polynucleic acid molecule as described above.

In some aspects, the disclosure relates to engineered viral genomes comprising a contiguous polynucleic acid molecule as described above. In some embodiments, the viral genome is an adeno-associated virus (AAV) genome, a lentivirus genome, an adenovirus genome, a herpes simplex virus (HSV) genome, a Vaccinia virus genome, a poxvirus genome, a Newcastle Disease virus (NDV) genome, a Coxsackievirus genome, a rheovirus genome, a measles virus genome, a Vesicular Stomatitis virus (VSV) genome, a Parvovirus genome, a Seneca valley viral genome, a Maraba virus genome, or a common cold virus genome.

In some aspects, the disclosure relates to virions comprising an engineered viral genome as described above.

In some aspects, the disclosure relates to methods of stimulating a cell-specific event in a population of cells. In some embodiments, the method comprises contacting a population of cells with a contiguous polynucleic acid molecule as described above, a vector as described above, an engineered viral genome as described above, or a virion as described above.

In some embodiments, the cell-specific event is regulated by: an endogenous transcription factor that binds and transactivates a regulatory component of at least one cassette; and/or transcriptional activity of the promoter fragment; and/or at least one endogenous microRNA that complements a microRNA target site of a response component of at least one cassette; or is regulated by: an endogenous transcription factor that binds and transactivates the transcription factor response element of the 5' regulatory component of at least one cassette; and/or transcriptional activity of the promoter fragment; and/or at least one endogenous microRNA that complements a microRNA target site of the 3' response component of at least one cassette.

In some embodiments, the population of cells comprises at least one target cell and at least one non-target cell.

In some embodiments, the target cell and the non-target cell differ in: (i) protein levels or activity of an endogenous transcription factor that binds and transactivates a regulatory component of at least one cassette; and/or (ii) transcriptional activity of the promoter fragment; and/or (iii) RNA levels or activity of at least one endogenous microRNA that complements a microRNA target site of a response component of at least one cassette; and wherein the differing protein levels or activity in (i) and/or transcriptional activity of the promoter fragment in (ii) and/or RNA levels or activity in (iii) causes the target cell and non-target cell to differ in expression levels of the output of the response component of at least one cassette thereby stimulating a cell-specific event.

In some embodiments, the target cell and the non-target cell differ in: (i) protein levels or activity of an endogenous transcription factor that binds and transactivates the transcription factor response element of a 5' regulatory component of at least one cassette; and/or (ii) transcriptional activity of the promoter fragment; and/or (iii) RNA levels of at least one endogenous microRNA that complements a microRNA target site of a 3' response component of at least one cassette; and wherein the differing protein levels in (i) and/or transcriptional activity of the promoter fragment in (ii) and/or RNA levels in (iii) causes the target cell and the non-target cell to differ in expression levels of the output of the 3' response component of at least one cassette thereby stimulating a cell-specific event.

In some embodiments, the expression levels of the output of the 3' response component differs between target cell types and non-target cell types by at least 2, at least 5, at least 10, at least 100, at least 1,000, or at least 10,000 fold.

In some embodiments, the cells of the target cell population are tumor cells and the cell-specific event is cell death. In some embodiments, the tumor cell death is mediated by immune targeting through the expression of activating receptor ligands, specific antigens, stimulating cytokines or any combination thereof.

In some embodiments, the cells of the target cell population are senescent cells and the cell-specific event is cell death.

In some embodiments, the method further comprises contacting the population of cells with prodrug or a non-toxic precursor compound that is metabolized by the output into a therapeutic or a toxic compound.

In some embodiments, the cells of the target cell population differentially express a factor relative to wild-type cells of the same type, and the cell-specific event is modulating expression levels of the factor.

In some embodiments, output expression ensures the survival of the target cell population while the non-target cells are eliminated due to lack of output expression and in the presence of an unrelated and unspecific cell death-inducing agent.

In some embodiments, the cells of the target cell population comprise a particular phenotype of interest such that output expression is limited to the cells of this particular phenotype.

In some embodiments, the cells of the target cell population are a cell type of choice and the cell-specific event is the encoding of a novel function, through the expression of a gene naturally absent or inactive in the cell type of choice.

In some embodiments, the population of cells comprises a multicellular organism. In some embodiments, the multicellular organism is an animal. In some embodiments, the animal is a human.

In some embodiments, the population of cells is contacted ex-vivo. In some embodiments, the population of cells is contacted in-vivo.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It is to be understood that the data illustrated in the drawings in no way limit the scope of the disclosure.

FIG. 1A. Schematic representing the various options of genetic interactions that can be implemented in a contiguous DNA molecule described herein. The thin bars and thick annotated features represent various functional DNA-encoded building blocks. Only DNA, microRNA (miR) and protein components are shown explicitly. The blunt arrows represent repression of gene expression by microRNA, which occurs at the mRNA level. mRNA is not shown explicitly, but it is implied that the presence of a microRNA target such as T-X and T-Y as a part of the DNA sequence will also lead to the presence of this same target in the transcribed mRNA, which would then be targeted by the miRNA input. Hollow pointed arrows indicate activation of gene expression. Full pointed arrows indicate gene expression (shown as a direct transition from DNA to protein, mRNA intermediate is not shown). Abbreviations are as follows: TF-A: an arbitrary transcription factor A; TF-B: an arbitrary transcription factor B; miR-X: an arbitrary microRNA X; miR-Y: an arbitrary microRNA Y; T-X: a sequence targeted by miR-X; T-Y: a sequence targeted by miR-Y; TF-A-RE: response recognized by an arbitrary transcription factor A; TF-B-RE: response element for an arbitrary transcription factor B; AA: auxiliary transactivator protein; AA-RE: a response element recognized by an auxiliary transactivator; Pmin: a minimal promoter with low intrinsic leakage; Output: an arbitrary protein or RNA-coding gene; PR-E: an arbitrary promoter or promoter fragment. FIG. 1B. The presence of microRNA targets according to option 3a and 3b resulted in very strong downregulation of the output expression, namely, more than 100-fold repression. Ctr miR stands for "Control" miRNA, a miRNA sequence that does not elicit effect either against miR-424 or miR-126 targets. The left bar in each grouping indicates an output gene containing a miR-424 target sequence and the right bar in each grouping represents an output gene containing the miR-126 target.

FIG. 3A. Specific implementations compatible with adeno-associated viral vectors (AAV). The divergent and the convergent variants were constructed, either without microRNA targets or with the microRNA targets indicated in the figure. Two different auxiliary transactivators (PIT-RelA fusion and PIT-VP16 fusion) were used. The contiguous DNA constructs were flanked with AAV2 ITRs (inverted terminal repeats) necessary for packing in the AAV virions. FIG. 3B. Comparison between the convergent and divergent variants in Huh-7 cells. mCherry fluorescence was measured when the DNA molecule was transiently transfected into the cells. The two bars on the left compare the convergent and divergent variant without miRNA targets. They showed comparable output expression level. The two bars on the right compare the divergent and the convergent variants that include miRNA target T-miR-424. The divergent variant clearly showed a much improved gene expression over the convergent variant.

FIG. 4A. Schematics of four different contiguous DNA cassettes that have been constructed. The virions containing different DNA cassettes are shaded in accordance with the miRNA target embedded in the cassette (no target; miR-126 target; miR-424 target; miR-122 target. Note that the data pertaining to the miR-122 target containing virion is only shown in FIGS. 6A-6B and FIGS. 7A-7C). The DNA payload implements the logic mechanism 'output' ~Sox9/10 AND Hnf1A/B AND NOT(MiR-X), where X=126 or 424 or 122; when no target is present, the DNA payload implements the mechanism 'output'~Sox9/10 AND Hnf1A/B. There are two different outputs: mCherry fluorescent reporter and an enzyme HSV-TK (thymidine kinase) that converts a non-toxic prodrug Ganciclovir to a toxic product leading to cell death. The bar chart shows measured mCherry expression in various cell lines (left to right in each grouping: HepG2, Huh7, HCT-116, Hela) infected with the virions carrying the respective DNA payload (Circuit Vectors, left to right: HNF1A/B AND SOX9/10, HNF1A/B AND SOX9/10 AND NOT(mir-126), HNF1A/B AND SOX9/10 AND NOT(mir-424)). The cell lines HepG2 and Huh7 express high levels of Sox9/10 and HNF1A/B without expression of either miRN-126 or miR-424, and therefore were expected to result in high output expression. Cell lines HCT-116 and HeLa do not express either Sox9/10 or HNF1A/B and therefore were expected to result in very low output expression. The data show that indeed, the virions caused very strong mCherry expression in cell lines HepG2 and Huh-7 and almost 1000-fold lower expression in cell lines HeLa and HCT-116, consistent with expectation. FIG. 4B. The schematic on the right shows the logic program controlling the output and leading to cell death when both Sox9/10 and HNF1A/B are highly expressed and the miRNA is not expressed. The bar chart on the left shows strong cell death when HepG2 cells (left bar in each grouping) were infected with the three types of virions and negligible cell death of HeLa cells (right bar in each groupin), as expected. Circuit vectors, left to right: HNF1A/B AND SOX9/10, HNF1A/B AND SOX9/10 AND NOT(mir-126), HNF1A/B AND SOX9/10 AND NOT(mir-424). The two bars labelled "constitutive cherry" show that the cells were not killed by AAV infection but via the toxic output. The bar chart in the middle shows that both cell lines (left: HepG2; right: Hela) were killed by constitutively expressed HSV-TK, therefore differential effect is due to the gene circuit DNA payload.

FIG. 5A. Schematics of the contiguous DNA cassettes. Two different pairs of insulators as well as a structure without insulators were implemented. FIG. 5B. Expression of the fluorescent output in two cell lines that were expected to result in high output expression (HuH-7 and HepG2) and a cell line that was not expected to lead to high expression, HCT-116. In general, the results were consistent with expectation. The pair of insulators A1/A3 showed a good combination of high output expression in the intended cell lines and low expression in the 'negative' cell line. For each set of bars: left, None; middle, A1/A3; right, F1/C3. FIG. 5C. Time course of output expression obtained from these integrated vectors in positive and negative cell lines. Good expression stability was observed over 60 days with the constructs using the pair of insulators A1/A3. Top line: Huh7; middle line: HepG2; bottom line: HCT-116.

FIG. 6A. Schematic outlined structure of the contiguous DNA cassettes (see also FIGS. 4A-4B). The program implemented by the gene circuit is HNF1A/B AND Sox9/10 AND NOT (miR-122). This was expected to result in high expression in HepG2 tumor cells and low expression in the mouse liver, due to high expression of miR-122 in the liver. AAV-DJ virions were generated with these contiguous cassettes. In addition contiguous cassettes without miRNA-122 targets was generated. Both contiguous cassette molecules generate mCherry output and serve to assess cell targeting specificity. The experimental workflow is exemplified under the DNA scheme. FIG. 6B. The mice were injected with luciferase and YFP-modified HepG2 cancer cells into the spleen. The cells disseminate to the liver, forming multiple tumor foci resembling clinical presentation of liver cancer. After the tumor was established, the virions were injected systemically via tail vein. A few days later the animals were euthanized and the liver tissue as well as embedded tumors were tested for the expression of the mCherry output protein. Specific expression is achieved when the "yellow" signal representing tumor cells is co-localized with the "mCherry" signal representing circuit output. The microscopy snapshots were taken from representative fresh liver slices. The images show, top to bottom, the phase contrast image of the slice; the location of the tumor; and the expression of the vector output. Left to right, a vector with constitutive mCherry expression; a vector implementing a program HNF1A/B AND Sox9/10; and a vector implementing a program HNF1A/B AND Sox9/10 AND NOT(miR-122). The two latter vectors implement divergent orientation in their contiguous DNA payload.

FIG. 7A. The contiguous DNA cassettes shown in FIG. 6A were modified to contain a gene encoding an HSV-TK enzyme as an output. FIGS. 7A-7B. The tumors were established in the mouse liver similar to the description in FIG. 6B. The AAV-DJ-typed vector was injected systemically in the tail vein twice; GCV administration started three days after the first injection, daily for the next 15 days. FIG. 7B. Plot showing tumor load in the whole liver at the time of termination, as assessed by whole-organ bioluminescence. The three groups include the mice injected with the viral vector alone, the ones treated with GCV alone, and the ones treated with a combination of viral injection and GCV. Only in the latter group was the tumor size greatly reduced compared to the control. Images on the right validate this assertion. FIG. 7C. The column "Whole liver bioluminescence" shows the luminescent signal from an entire liver post-mortem. The second column shown phase images of representative liver slices. The third column shows representative slices of fresh liver, with signal indicating tumor foci. Only the mice treated with the viral vector and with GCV exhibit greatly reduced tumor load, as expected.

DETAILED DESCRIPTION

Classifier gene circuits are artificial gene networks or circuits (sets of engineered interacting gene and genetic elements) able to transduce specific combinations of cytoplasmic molecular features into a specific cell response, for example activating a gene only in cells where certain molecules are absent or present, according to programmable rules (Xie Z. et al., Science. 2011 Sep. 2; 333(6047): 1307-11; Benenson Y., Nat. Rev. Genet. 2012 Jun. 12; 13(7): 455-468). The ability to precisely control cell behavior offers great promise to research, biotechnological and biomedical applications. However, the potential of this technology for therapeutic applications is hindered by the size and complexity of the genetic circuits required to implement therapeutically-relevant action and by the fact that such circuits are not inherently compatible with therapeutically-accepted modalities such as viral vectors and engineered cells. Instead, most—if not all—reports on classifier circuits have disclosed sets of plasmids delivered to cultured cells using transient transfection, rather than by a viral carrier with potential medical utility.

Indeed, medical translation of these developments requires efficient DNA delivery to somatic cells in vivo, which is currently implemented with the help of specialized viral vectors and, increasingly, non-viral delivery vectors, selected on the basis of administration route, tissue to be targeted, and other specific requirements. Combining existing classifier circuit technologies with these vectors remains a serious challenge. As the circuit complexity (the number of input features and the number of circuit genes) required for specific cell targeting increases, circuit packaging in viral carriers becomes progressively harder for at least two reasons.

First, any viral delivery vehicle has limited cargo capacity, making it difficult to accommodate all the genetic components required for circuit functionality and the therapeutic outputs of interest. Likewise, non-viral vectors may deteriorate in their performance as the DNA size increases due to the increased size of the particle complexes formed between DNA and the packaging substance.

Second, the risk of context effects (e.g., transcriptional read-through, promoter context, junction composition) increases with the number of independent transcriptional units on the same vector. Context effects are hard to predict and can affect circuit performances or even change the expected behavior altogether.

Figure 1B:
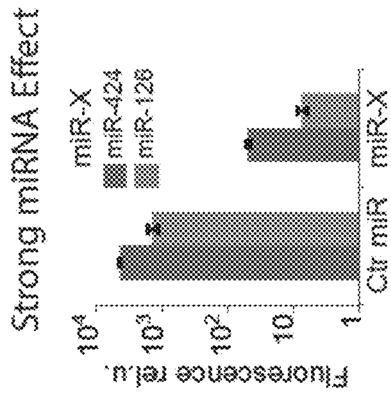
FIGS. 1A-1B.

Disclosed herein are contiguous polynucleic acid molecules that encode classifier gene circuits (FIG. 1) compatible with commonly used gene therapy viral and non-viral vectors. Also disclosed herein are methods of implementing complex multi-input control over the expression of a gene of interest in a population of cells.

Compositions of Contiguous Polynucleic Acid Molecules

In some aspects, the disclosure relates to contiguous polynucleic acid molecules comprising at least one expression cassette. As used herein, the term "contiguous polynucleic acid molecule" refers to a single, continuous nucleic acid molecule (i.e., each expression cassette is encoded on a single polynucleic acid molecule) or two complementary continuous nucleic acid molecules (i.e., each expression cassette is encoded on a double-stranded polynucleic acid molecule comprising two complementary strands). In some embodiments, the contiguous polynucleic acid is an RNA (e.g., single-stranded or double-stranded). In some embodiments, the contiguous polynucleic acid is a DNA (e.g., single-stranded or double-stranded). In some embodiments, the contiguous polynucleic acid is a DNA:RNA hybrid.

Figure 2A:
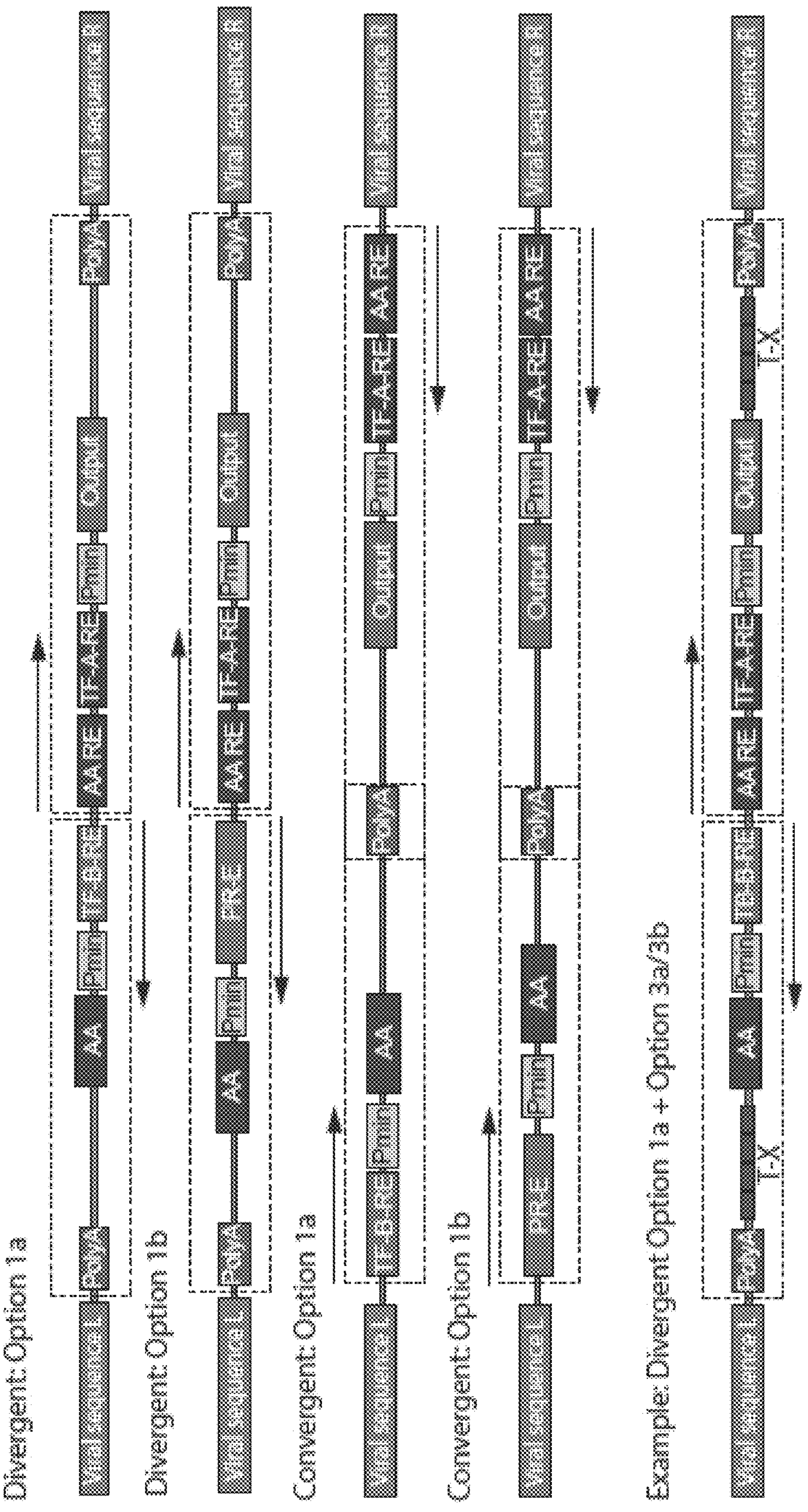
FIGS. 2A-2B. Contiguous DNA structure variants. Gene circuits depicted as in FIG. 1A, as implemented in contiguous DNA molecules. Each structure variant represents a different multi-input program; divergent and convergent configurations are shown. Abbreviations are as follows: Viral sequence L: any sequences that are specific to viral vectors and need to be in the vector irrespective of the gene circuit payload, including inverted terminal repeat (ITR), Long terminal repeat (LTR), Psi sequence, packaging signals, genes required for virus replication and packaging in the case of oncolytic vectors, etc.; Viral sequence R: same as Viral sequence L, but flanking the contiguous DNA cassette from the right; PolyA: polyadenylation signal and 3'-untranslated region (3'-UTR) of a gene; Rep gene: a vector-specific gene or genes that trigger viral vector replication; TF-A: an arbitrary transcription factor A; TF-B: an arbitrary transcription factor B; miR-X: an arbitrary microRNA X; miR-Y: an arbitrary microRNA Y; T-X: a sequence targeted by miR-X; T-Y: a sequence targeted by miR-Y; TF-A-RE: response element for an arbitrary transcription factor A; TF-B-RE: response element for an arbitrary transcription factor B; AA: auxiliary transactivator protein; AA-RE: A response element that binds an auxiliary transactivator; Pmin: a minimal promoter with low intrinsic leakage; Output: an arbitrary protein or RNA-coding gene; PR-E: an arbitrary promoter or promoter fragment.
Figure 2B:
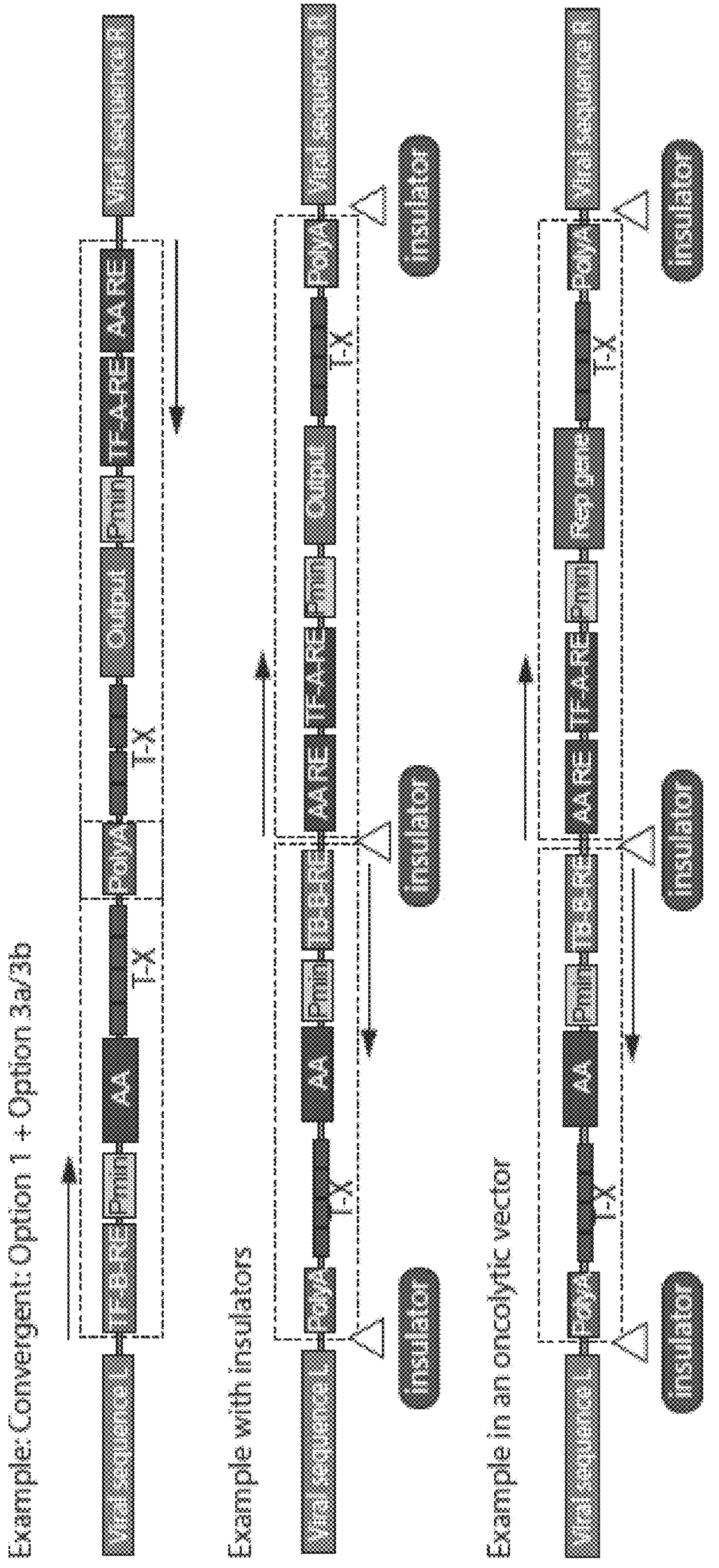
Figure 3A:
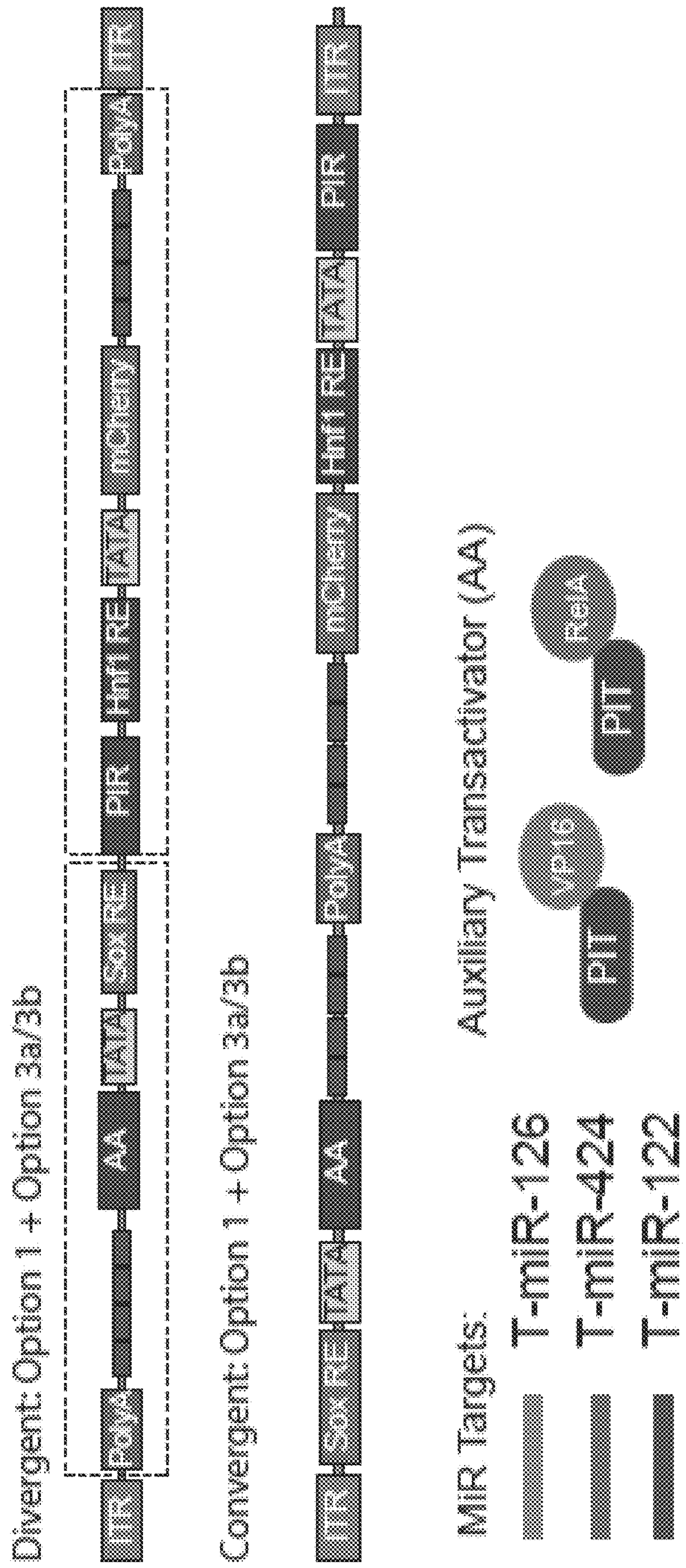
FIGS. 3A-3B.
Figure 3B:
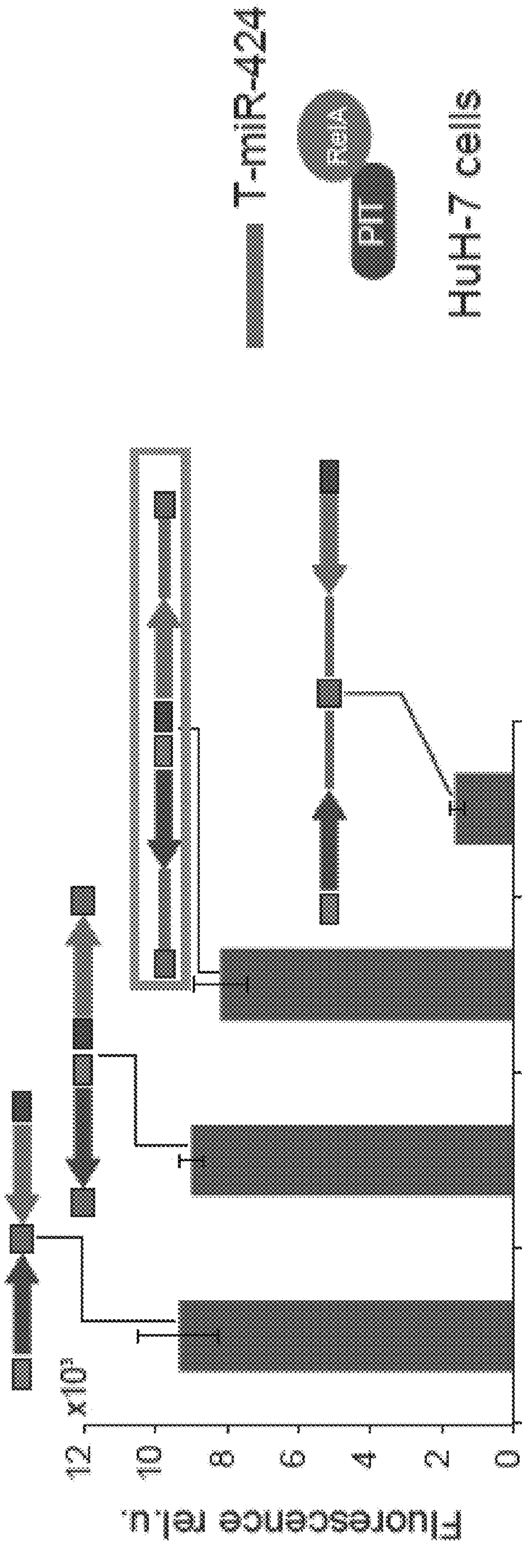

In some embodiments, a contiguous polynucleic acid molecule comprises at least two cassettes. In some embodiments, at least two cassettes are in a divergent orientation. The term "divergent orientation," as used herein, refers to a configuration in which: (i) transcription of a first cassette and a second cassette proceeds on differing strands of the contiguous polynucleic acid molecule and (ii) transcription of the first cassette is directed away from the second cassette and transcription of the second cassette is directed away from the first cassette. FIG. 2 provides examples of various divergent configurations.

In some embodiments, two cassettes are in a convergent orientation. As used herein, the term "convergent orientation" refers to a configuration in which: (i) transcription of a first cassette and a second cassette proceeds on differing strands of the contiguous polynucleic acid molecule and (ii) transcription of the first cassette is directed toward the second cassette and transcription of the second cassette is directed toward the first cassette. In some embodiments, two convergent cassettes share a polyadenylation sequence. FIG. 2 provides examples of various convergent configurations.

In some embodiments, at least two cassettes are in a head-to-tail orientation. As used herein, the term "head-to-tail" refers to a configuration in which: (i) transcription or translation of the first cassette and the second cassettes proceeds on the same strand of the contiguous polynucleic acid molecule and (ii) transcription or translation of the first cassette is directed toward the second cassette and transcription or translation of the second cassette is directed away from the first cassette (5' . . . → . . . → . . . 3').

As used herein, the term "expression cassette" or "cassette" are used interchangeably and refer to a polynucleic acid comprising at least one regulatory component and at least one response component, wherein the regulatory component modulates transcription of the response component, RNA levels of the response component, and/or protein generation from the response component.

In some embodiments, at least one cassette of a contiguous polynucleic acid molecule is flanked by an insulator. Insulators are nucleic acid sequences, that when bound by insulator-binding proteins, shield a regulatory component or a response component from the effects of other nearby regulatory elements. For example, flanking the cassettes of a contiguous polynucleic acid molecule can shield each cassette from the effects of regulatory elements of the other cassettes. Examples of insulators are known to those having skill in the art.

Regulatory Component

A cassette of a contiguous polynucleic acid molecule comprises at least one regulatory component. A regulatory component may comprise one or more of a transactivator response element, a transcription factor response element, a promoter element, or a minimal promoter. One having skill in the art will appreciate that these elements may be oriented in various configurations. For example, a transactivator response element may be 5' or 3' to a promoter element and/or transcription factor response element; a transcription factor response element may be 5' or 3' to a promoter element and/or transactivator response element; a promoter element may be 5' or 3' to a transcription factor response element and/or a transactivator response element.

The term "transactivator" or "transactivator protein," as used herein, refer to a protein encoded on the contiguous polynucleic acid molecule that transactivates expression of an output (i.e., gene of interest) and binds to a transactivator response element that is operably linked to the nucleic acid encoding an output (i.e., gene of interest). A transactivator response element is "operably linked" to a nucleic acid encoding an output when it is in a correct functional location and orientation in relation to the nucleic acid sequence it regulates to control ("drive") transcriptional initiation and/or expression of that sequence. In some embodiments, the transactivator binds and transactivates the transactivator response element independently (i.e., in the absence of any additional factor). In other embodiments, the transactivator binds and transactivates the transactivator response element only in the presence of a transcription factor bound to the transcription factor response element.

In some embodiments, a transactivator protein comprises a DNA-binding domain. In some embodiments, the DNA-binding domain is engineered (i.e., not naturally-occurring) to bind a DNA sequence that is distinct from naturally-occurring sequences. Examples of DNA-binding domains are known to those having skill in the art and include, but are not limited to, DNA-binding domains derived using zinc-finger technology or TALEN technology or from mutant response regulators of two-component signaling pathways from bacteria.

In some embodiments, a DNA-binding domain is derived from a mammalian protein. In other embodiments a DNA binding domain is derived from a non-mammalian protein. For example, in some embodiments, a DNA-binding domain is derived from a protein originating in bacteria, yeast, or plants. In some embodiments, the DNA-binding domain requires are additional component (e.g., a protein or RNA) to target the transactivator response element. For example, in some embodiments, the DNA-binding domain is that of a CRISPR/Cas protein (e.g., Cas1, Cas2, Cas3, Cas5, Cas4, Cas6, Cas7, Cas8a, Cas8b, Cas8c, Cas9, Cas10, Cas10d, Cse1, Cse2, Csy1, Csy2, Csy3, Csm2, Cmr5, Csx10, Csx11, Csf1, Cpf1, C2c1, C2c2, C2c3) which requires the additional component of a guide RNA to target the transactivator response element.

In some embodiments, the transactivator protein is derived from a naturally-occurring transcription factor, wherein the DNA-binding domain of the naturally-occurring transcription factor has been mutated, resulting in an altered DNA binding specificity relative to the wild-type transcription factor. In some embodiments, the transactivator is a naturally-occurring transcription factor.

In some embodiments, a transactivator protein further comprises a transactivating domain (i.e., a fusion protein comprising a DNA binding domain and a transactivating domain). As used herein, the term "transactivating domain" refers to a protein domain that functions to recruit transcriptional machinery to a minimal promoter. In some embodiments, the transactivating domain does not trigger gene activation independently. In some embodiments, a transactivating domain is naturally-occurring. In other embodiments, a transactivating domain is engineered. Examples of transactivating domains are known to those having skill in the art and include, but are not limited to RelA transactivating domain, VP16, VP48, and VP64.

In some embodiments, the transactivator of at least one cassette is tTA, rtTA, PIT-RelA, PIT-VP16, ET-VP16, ET-RelA, NarLc-VP16, or NarLc-RelA. See e.g., Angelici B. et al., Cell Rep. 2016 Aug. 30; 16(9): 2525-2537.

In some embodiments, the regulatory component comprises a transactivator response element. The "transactivator response element" can comprise a minimal DNA sequence that is bound and recognized by a transactivator protein. In some embodiments the transactivator response elements comprises more than one copy (i.e., repeats) of a minimal DNA sequence that is bound and recognized by a transactivator protein. In some embodiments, a transactivator response element comprises at least 2, at least 3, at least 4, at least 5, at least 6, at least 7, at least 8, at least 9, or at least 10 repeats of a minimal DNA sequence that is bound and recognized by a transactivator protein. In some embodiments the repeats are tandem repeats. In some embodiments, the transactivator response element comprises a combination of minimal DNA sequences. In some embodiments, minimal DNA sequences are interspersed with spacer sequences. In some embodiments, a spacer sequence is 1, 2, 3, 4, 5, 6, 7, 8, 9, 10, 11, 12, 13, 14, 15, 16, 17, 18, 19, 20, or greater than 20 nucleotides in length.

In some embodiments, the regulatory component comprises a transcription factor response element. The term "transcription factor response element" refers to a DNA sequence that is bound and recognized by a transcription factor. As used herein, the term "transcription factor" refers to a protein that is not encoded on the contiguous polynucleic acid that modulates gene transcription. In some embodiments, a transcription factor is a transcription activator (i.e., increases transcription). In other embodiments, a transcription factor is a transcription inhibitor (i.e., inhibits transcription). In some embodiments, a transcription factor is an endogenous transcription factor of a cell.

The "transcription factor response element" can comprise a minimal DNA sequence that is bound and recognized by a transcription factor. In some embodiments the transcription factor response element comprises more than one copy (i.e., repeats) of a minimal DNA sequence that is bound and recognized by a transcription factor. In some embodiments, a transcription factor response element comprises at least 2, at least 3, at least 4, at least 5, at least 6, at least 7, at least 8, at least 9, or at least 10 repeats of a minimal DNA sequence that is bound and recognized by a transcription factor. In some embodiments the repeats are tandem repeats. In some embodiments, the transcription factor response element comprises a combination of minimal DNA sequences. In some embodiments, minimal DNA sequences are interspersed with spacer sequences. In some embodiments, a spacer sequence is 1, 2, 3, 4, 5, 6, 7, 8, 9, 10, 11, 12, 13, 14, 15, 16, 17, 18, 19, 20, or greater than 20 nucleotides in length. In some embodiments, the transcription factor response element is unique (i.e., the contiguous polynucleic acid includes only one copy of the transcription factor response element). In other embodiments, the transcription factor response element is not unique.

In some embodiments, a regulatory component comprises a promoter element. In some embodiments, the promoter element comprises a transcription factor response element and a minimal promoter. In some embodiments, the promoter element comprises a mammalian promoter or promoter fragment. In some embodiments, the mammalian promoter or promoter fragment is unique (i.e., the contiguous polynucleic acid includes only one copy of the mammalian promoter or promoter fragment). In other embodiments, the mammalian promoter or promoter fragment is not unique.

In some embodiments, a regulatory component comprises a minimal promoter. As used herein, the term "minimal promoter" refers to a nucleic acid sequence that is necessary but not sufficient to initiate expression of an output. In some embodiments, a minimal promoter is naturally occurring. In other embodiments, a minimal promoter is engineered, such as by altering and/or shortening a natural occurring sequence, combining natural occurring sequences, or combining naturally occurring sequences with non-naturally occurring sequences; in each case an engineered minimal promoter is a non-naturally occurring sequence. In some embodiments, the minimal promoter is engineered from a viral or non-viral source. Examples of minimal promoters are known to those having skill in the art.

In some embodiments, a regulatory component comprises a transactivator response element, a transcription factor response element, and a minimal promoter. In some embodiments, the regulatory component of a cassette comprises, from 5' to 3': a transactivator response element, a transcription factor response element, and a minimal promoter. In some embodiments, a regulatory component comprises from 5' to 3': a transcription factor response element, a transactivator response element, and a minimal promoter.

In some embodiments, the regulatory component of a cassette comprises a transactivator response element and a promoter element. In some embodiments, the regulatory component of a cassette comprises, from 5' to 3': a transactivator response element and a promoter element. In some embodiments, the regulatory component of a cassette comprises a transactivator response element, a promoter element and a minimal promoter. In some embodiments, the regulatory component of a cassette comprises, from 5' to 3': a transactivator response element, a promoter element and a minimal promoter. In some embodiments, the regulatory component of a cassette comprises, from 5' to 3': a promoter element and a transactivator response element. In some embodiments, the regulatory component of a cassette comprises, from 5' to 3': a promoter element, a transactivator response element and a minimal promoter. In some embodiments, the promoter element is a mammalian promoter. In some embodiments, the promoter element is a promoter fragment.

In some embodiments, a regulatory component (e.g., a transactivator response element, and/or a transcription factor response element, and/or a promoter element, and/or a minimal promoter) is operably linked to a nucleic acid encoding a transactivator protein and/or an output. A regulatory component is considered to be "operably linked" when it is in a correct functional location and orientation in relation to a nucleic acid sequence it regulates to control ("drive") transcriptional initiation and/or expression of that sequence. A regulatory component may be bound by a transcription factor and/or transactivator protein that increases or decreases the expression of the transactivator protein and/or output.

Response Component

A cassette of a contiguous polynucleic acid molecule comprises at least one response component. In some embodiments, a response component comprises a nucleic acid sequence encoding an output or gene of interest. In some embodiments, the output is an RNA molecule. In some embodiments, the RNA molecule is a mRNA encoding for a protein. In some embodiments, the output is a non-coding RNA molecule. Examples of non-coding RNA molecules are known to those having skill in the art and include, but are not limited to, include transfer RNAs (tRNAs), ribosomal RNAs (rRNAs), microRNAs, siRNAs, piRNAs, snoRNAs, snRNAs, exRNAs, scaRNAs, and long ncRNAs.

In some embodiments, the output is a therapeutic molecule (i.e., related to the treatment of disease), such as a therapeutic protein or RNA molecule. Examples of therapeutic molecules include, but are not limited to, antibodies (e.g., monoclonal or polyclonal; chimeric; humanized; including antibody fragments and antibody derivatives (bispecific, trispecific, scFv, and Fab)), enzymes, hormones, inflammatory molecules, anti-inflammatory molecules, immunomodulatory molecules, anti-cancer molecules, short-hairpin RNAs, short interfering RNAs and microRNAs. Specific examples of the foregoing classes of therapeutic molecules are known in the art, any of which may be used in accordance with the present disclosure.

In some embodiments, the output is a detectable protein, such as a fluorescent protein.

In some embodiments, the output is a cytotoxin. As used herein, the term "cytotoxin" refers to a substance that is toxic to a cell. For example, in some embodiments, the output is a cytoxic protein. Examples of cytotoxic proteins are known to those having skill in the art and include, but are not limited to, granulysin, perforin/granzyme B, the Fas/Fas ligand, and various cytokines/chemokines (e.g., IL-2, IL-5, IL-6, IL-10, IL-12, IL-13, IL-15, IL-18, CCR3, CXCR3, CXCR4, and CCR10).

In some embodiments, the output is an enzyme that catalyzes activation of a prodrug. Examples of enzymes that catalyze prodrug activation are known to those having skill in the art, and include, but are not limited to carboxylesterases, acetylcholinesterases, butyrlylcholinesterases, paraxonases, matrix metalloproteinases, alkaline phosphatases, (3-glucuronidases, valacyclovirases, prostate-specific antigens, purine-nucleoside phosphorylases, carboxypeptidases, amidases, β-lactamases, β-galactosidases, and cytosine deaminases. See e.g., Yang Y. et al., Enzyme-mediated hydrolytic activation of prodrugs. Acta. Pharmaceutica. Sinica B. 2011 October; 1(3): 143-159. Likewise, various prodrugs are known to those having skill in the art and include, but are not limited to, acyclovir, allopurinaol, azidothymidine, bambuterol, becampicillin, capecetabine, captopril, carbamazepine, carisoprodol, cyclophosphamide, diethylstilbestrol diphosphate, dipivefrin, enalapril, famciclovir, fludarabine triphosphate, fluorouracil, fosmaprenavir, fosphentoin, fursultiamine, gabapentin encarbil, ganciclovir, gemcitabine, hydrazide MAO inhibitors, leflunomide, levodopa, methanamine, mercaptopurine, mitomycin, molsidomine, nabumetone, olsalazine, omeprazole, paliperidone, phenacetin, pivampicillin, primidone, proguanil, psilocybin, ramipril, S-methyldopa, simvastatin, sulfasalazine, sulindac, tegafur, terfenadine, valacyclovir, valganciclovir, and zidovudine.

In some embodiments, the output is an immunomodulatory protein and/or RNA. As used herein, the term "immunomodulatory protein" (or immunomodulatory RNA) refers to a protein (or RNA) that modulates (stimulates (i.e., an immunostimulatory protein or RNA) or inhibits, (i.e., an immunoinhibitory protein or RNA)) the immune system by inducing activation and/or increasing activity of immune system components. Various immunomodulatory proteins are known to those having skill in the art. See e.g., Shahbazi S. and Bolhassani A. Immunostimulants: Types and Funtions. J. Med. Microbiol. Infec. Dis. 2016; 4(3-4): 45-51. In some embodiments, the immunomodulatory protein is a cytokine or a colony stimulating factor.

In some embodiments, the output is a DNA-modifying factor. As used herein the term "DNA-modifying factor" refers to a factor that alters the structure of DNA and/or alters the sequence of DNA (e.g., by inducing recombination or introduction of mutations). In some embodiments, the DNA-modifying factor is a gene encoding a protein intended to correct a genetic defect, a DNA-modifying enzyme, and/or a component of a DNA-modifying system. In some embodiments, the DNA-modifying enzyme is a site-specific recombinase, homing endonuclease, or a protein component of a CRISPR/Cas DNA modification system.

In some embodiments, the output is a cell-surface receptor. In some embodiments, the output is a kinase.

In some embodiments, the output is a gene expression-regulating factor. The term "gene expression-regulating factor," as used herein, refers to any factor that, when present, increases or decreases transcription of at least one gene. In some embodiments, the gene expression-regulating factor is a protein. In some embodiments, the gene expression-regulating factor is an RNA. In some embodiments, the gene expression-regulating factor is a component of a multi-component system capable of regulating gene expression.

In some embodiments, the output is an epigenetic modifier. The term “epigenetic modifier,” as used herein, refers to a factor (e.g., protein or RNA) that increases, decreases, or alters an epigenetic modification. Examples of epigenetic modifications are known to those of skill in the art and include, but are not limited to, DNA methylation and histone modifications.

In some embodiments, the output is a factor necessary for vector replication. Examples of factors necessary for vector replication are known to those having skill in the art.

In some embodiments, the response component comprises a nucleic acid sequence encoding a transactivator.

In some embodiments, the response component comprises a polycistronic expression element. The term “polycistronic response element,” as used herein, refers to a nucleic acid sequence that facilitates the generation of two or more proteins from a single mRNA. A polycistronic response element may comprise a polynucleic acid encoding an internal recognition sequence (IRES) or a 2A peptide. See e.g., Liu et al., Systematic comparison of 2A peptides for cloning multi-genes in a polycistronic vector. Sci. Rep. 2017 May 19; 7(1): 2193.

In some embodiments, a response component comprises the nucleic acid sequence encoding an output, a transactivator, and a polycistronic expression element, wherein transcription of the response component generates a single mRNA. In some embodiments, the output and the transactivator are separated by the polycistronic expression element.

In some embodiments, the response component comprises at least one polyadenylation sequence. In some embodiments the polyadenylation sequence is suitable for transcription termination and polyadenylation in mammalian cells.

In some embodiments, a response component comprises at least one microRNA target site. In some embodiments, the response component comprises at least 1, at least 2, at least 3, at least 4, at least 5, or at least 6 microRNA target sites. MicroRNAs are a class of small non-coding RNAs that are typically 21-25 nucleotides in length is to downregulate the levels of RNAs to which they bind in a variety of manners, including translational repression, mRNA cleavage, and deadenylation.

The term “microRNA target site,” as used herein, refers to a sequence that complements and is regulated by a microRNA. A microRNA target site may have at least 25%, at least 30%, at least 40%, at least 50%, at least 60%, at least 70%, at least 80%, at least 85%, at least 90%, at least 95%, at least 96%, at least 97%, at least 98%, at least 99%, or 100% identity to the microRNA that binds and regulates the microRNA target site.

In some embodiments, at least one microRNA target site is 3' to the output. In some embodiments, at least one microRNA target site is 5' to the output.

In some embodiments, a response component comprises from 5' to 3': an output and at least one microRNA target site. In some embodiments, a response component comprises from 5' to 3': a nucleic acid sequence encoding a transactivator protein and at least one microRNA target site. In some embodiments, a response component comprises from 5' to 3': a nucleic acid sequence encoding a transactivator protein, a nucleic acid sequence encoding an output, and at least one microRNA target site.

In some embodiments, multiple cassettes of a contiguous polynucleic acid molecule comprise at least one microRNA target site. In some embodiments, each microRNA target site of a contiguous polynucleic acid is unique (i.e., the contiguous polynucleic acid includes only one copy of the microRNA target). In some embodiments, a contiguous polynucleic acid molecule comprises at least two cassettes that each comprise at least one microRNA target site that is the same nucleic acid sequence. In some embodiments, a contiguous polynucleic acid molecule comprises at least two cassettes that each comprise at least one microRNA target site, wherein at least one microRNA target site of each cassette comprises a different nucleic acid sequence that is regulated by the same microRNA. For example, a first cassette may comprise microRNA target site X and a second cassette may comprise microRNA target site Y and microRNA Z regulates target site X and target site Y.

In some embodiments, a contiguous polynucleic acid molecule comprises at least one cassette, wherein the cassette comprises: (i) a 5' regulatory component comprising a transactivator response element, a transcription factor response element, and a minimal promoter; and (ii) a 3' response component comprising an output, a transactivator, and an optional polycistronic expression element, wherein the output and the transactivator are optionally separated by the polycistronic expression element; wherein transcription of the response component generates a single mRNA; and wherein the transactivator of (ii), when expressed as a protein, binds and transactivates the transactivator response element of (i).

In some embodiments, a contiguous polynucleic acid molecule encodes at least two cassettes, wherein: (i) at least one cassette comprises: a 5' regulatory component comprising a transactivator response element, a transcription factor response element, and a minimal promoter and a 3' response component comprising an output; and (ii) at least one cassette comprises: a promoter element operably linked to a nucleic acid sequence encoding a transactivator protein; and wherein the transactivator of (ii), when expressed as a protein, binds and transactivates the transactivator response element of (i).

Other Compositions

In other aspects, the disclosure relates to compositions of vectors. In some embodiments, a vector comprises a contiguous polynucleic acid molecule described above.

In other aspects, the disclosure relates to compositions of engineered viral genomes. In some embodiments, the viral genome comprises a contiguous polynucleic acid molecule described above. In some embodiments, the viral genome is an adeno-associated virus (AAV) genome, a lentivirus genome, an adenovirus genome, a herpes simplex virus (HSV) genome, a Vaccinia virus genome, a poxvirus genome, a Newcastle Disease virus (NDV) genome, a Coxsackievirus genome, a rheovirus genome, a measles virus genome, a Vesicular Stomatitis virus (VSV) genome, a Parvovirus genome, a Seneca valley viral genome, a Maraba virus genome, or a common cold virus genome.

In other aspects, the disclosure relates to compositions of virions. As used herein, the term “virion” refers to an infective form of a virus that is outside of a host cell (e.g., comprising a DNA/RNA genome and a protein capsid). In some embodiments, a virion comprises the engineered viral genome described above.

Methods of Stimulating a Cell-Specific Event

In other aspects, the disclosure relates to methods of stimulating a cell-specific event in a population of cells. In some embodiments, the method comprises contacting a population of cells with a contiguous polynucleic acid molecule described above, a vector described above, an engineered viral genome described above, or a virion described above, wherein the cell-specific event is regulated by at least one endogenous transcription factor and/or at least one endogenous microRNA.

In some embodiments, the contacting with the host cell with a contiguous polynucleic acid molecule described above or a vector described above occurs via a non-viral delivery method. Examples include, but are not limited to, transfection (e.g., DEAE dextran-mediated transfection, $CaPO_4$-mediated transfection, lipid-mediated uptake, PEI-mediated uptake, and laser transfection), transformation (e.g., calcium chloride, electroporation, and heat-shock), gene transfer, and particle bombardment.

In some embodiments, the population of cells is contacted ex-vivo (i.e., a population of cells is isolated from an organism, and the population of cells is contacted outside of the organism). In some embodiments, the population of cells is contacted in-vivo.

As used herein, the term "endogenous"—in the context of a cell—refers to a factor (e.g., protein or RNA) that is found in the cell in its natural state. In some embodiments, an endogenous transcription factor may bind and activate a promoter element of a regulatory component of at least one cassette (e.g., a transcription factor response element). In some embodiments, an endogenous microRNA may complement a microRNA target site of a regulatory component or response component of at least one cassette.

In some embodiments, a "transactivator" and corresponding "transactivator response element" will be selected such that the transactivator will specifically bind to the "transactivator response element" but bind as little as possible to response elements naturally present in the cell. In some embodiments, the DNA binding domain of a transactivator protein will not efficiently bind native regulatory sequences present in the cell and, therefore, will not trigger excessive side effects.

In some embodiments, the population of cells comprises at least one target cell and at least one non-target cell. A target cell and a non-target cell type differ in levels of at least one endogenous transcription factor and/or the expression strength of at least one endogenous promoter or its fragment and/or at least one endogenous microRNA. In some embodiments a target cell and a non-target cell are different cell types. For example, in some embodiments, a target cell is a cancerous cell and a non-target cell is a non-cancerous cell. Likewise, in some embodiments, a target cell is a hepatocyte and a non-target cell is a non-hepatocyte (e.g., a myocyte). In other embodiments, a target cell and a non-target cell are the same cell-type (e.g., both are hepatocytes), but nonetheless, differ in levels of at least one endogenous transcription factor and/or at least one endogenous microRNA. For example, a target cell may be a senescent muscle cell and a non-target cell may be a non-senescent muscle cell.

In some embodiments, the expression levels of the output of the response component differs between target cells and non-target cells by at least 2, at least 5, at least 10, at least 100, at least 1,000, or at least 10,000 fold.

In some embodiments, the cells of the target cell population are tumor cells and the cell-specific event is cell death. In some embodiments, the cells of the target cell population are senescent cells and the cell-specific event is cell death. In some embodiments, the cell death is mediated by immune targeting through the expression of activating receptor ligands, specific antigens, stimulating cytokines, or any combination thereof. In some embodiments, the method further comprises contacting the population of cells with a prodrug or a non-toxic precursor compound that is metabolized by the output into a therapeutic or a toxic compound.

In some embodiments, the cells of the target cell population differentially express a factor relative to wild-type cells of the same type and the cell-specific event is modulating expression levels of the factor.

In some embodiments, output expression ensures the survival of the target cell population while the non-target cells are eliminated due to lack of output expression and in the presence of a cell death-inducing agent. In other embodiments, the output ensures the survival of the non-target cell population while the target cells are eliminated due to output expression and in the presence of a cell death-inducing agent.

In some embodiments, the cells of the target cell population comprise a particular phenotype of interest such that output expression is limited to the cells of this particular phenotype.

In some embodiments, the cells of the target cell population are a cell type of choice and the cell-specific event is the encoding of a novel function, through the expression of a gene naturally absent or inactive in the cell type of choice.

In some embodiments, the population of cells comprises a multicellular organism. In some embodiments, the multicellular organism is an animal. In some embodiments, the animal is a human.

Advances Over the Prior Art

The compositions and methods disclosed herein represent advances over those of the prior art in various ways. Examples of these advances are provided below.

First, the approaches and methods described here exhibit increased precision. The ability to sense multiple highly informative molecules and combine their information allows to one restrict expression more precisely than using previously described natural tissue-specific promoters (usually expressed to different degrees in multiple tissues/cell types) or detargeting.

Second, the circuit architectures described herein show excellent dynamic range with tight Off and full expression comparable with strong constitutive promoters. This approach outcompetes classic transcriptional targeting, which often is plagued by weak and leaky expression. Strong absolute expression is key for the success of many gene therapies and high dynamic range is particularly important in the targeting of toxic genes (e.g., cancer suicide therapy).

Third, the structure of the circuits described herein is inherently modular (i.e. individual sensing sequences can be swapped to change the circuit specificity) and single signals are combined in a predictable way. As a result, single sensors can be combined according to the growing TFs and miRNA expression datasets to rationally design vectors with different specificities.

Moreover, these approaches can be used in the development of new gene and cell therapies (GCT) with improved specificity and higher efficacy. The logic circuit can be programmed to sense specific conditions and respond with a gene, therapeutic protein, corrective miRNA or with a multi-pronged combination of outputs. The programmable inputs, compact size and resulting ability to fit in a number of different viral vectors opens a wide variety of applications. The circuit can be packaged in the most appropriate AAV serotype and programmed to drive a functional gene only in the tissue of interest for precise somatic gene therapy. In a variant of this application, suicide gene therapy, a killing gene is expressed specifically in cancer cells and not in other healthy tissues in the body, as is described herein for specific targeting of hepatocellular carcinoma. This represents an ideal benchmark for the technology since it requires high expression levels in the cancer cells coupled to tight control in the other tissue where leaky expression can lead to toxic effects.

The circuits are small enough to be packaged in many oncolytic viruses (e.g., Adenovirus, HSV) without compromising the replication machinery, and thus can easily be used to precisely target virus replication in cancer cells. The circuit designs described herein can also be used in conjunction with lentiviral vectors for the ex-vivo engineering of cells to be used as stem cells or in immune therapy. In this case the circuit is designed to perform a specific genetic program only when certain in vivo conditions are met. As an example, stem cells might be transduced with a circuit as described herein, differentiated and selected in vitro; and the differentiated cells reinfused in the patient where the circuit monitors continuously the state of key pluripotency markers, killing the cell upon their appearance to avoid teratoma formation. The demonstration that the circuits described herein can be inserted between insulators and packaged in lentiviral particles with no significant effect on the circuit performance represents a first conceptual proof in this direction.

The compositions and methods disclosed herein represent specific advancements in the following fields:

Targeted expression of a gene of interest in gene therapy: Restricting the expression of a gene of interest (GOI) to a tissue/cell type of interest remains an open challenge in viral therapy. The problem is particularly acute, for example, in (i) cancer viral therapy due to high similarity between healthy and cancerous tissues and (ii) indications where the GOI has to be very tightly regulated due to adverse side effects in unintended tissues.

The primary approach to control the specificity of genes of interest embedded in a viral vector in the prior art is "transcriptional targeting" (Dorer D. E. and Nettelbeck D. M., Adv. Drug Deliv. Rev. 2009. 61(7-8): 554-571; Robson T. and Hirst D. G., J. Biomed. Biotechnol. 2003; 2003(2): 110-137; Navarro S. A. et al., Expert Opin. Ther. Pat. 2016 September; 26(9): 1095-1104). In this approach the GOI is placed under the control of a cancer-specific or tissue-specific promoter. The shortcomings of this method are numerous. For example, this approach has limited specificity. Promoters that are defined as "specific" are in fact often expressed in multiple tissues. This is particularly true for so called "cancer-specific promoters" since they are usually linked to overexpression of genes that are physiological in other tissues. In addition, this approach is also characterized by very low expression differences between the targeted tissue or cell type and those that are not supposed to be targeted. The majority of tissue- or cancer-specific promoters are both weak and rather leaky (e.g. AFP promoter, a commonly used tissue-specific promoter, is 500 fold less active than CAG) (Kanegae Y. et al., Nucleic Acids Res. 2011 January; 39(2): e7). This low difference in expression limits one's ability to restrict expression of strongly cytotoxic genes and proteins needed in high dosage to only those cells that require them. Proposed solutions to increase the strength of selective promoters include two-step transcriptional amplification (TSTA) (Iyer M. et al., Proc. Natl. Acad. Sci. U.S.A. 2001 Dec. 4; 98(25): 14595-14600; U.S. Pat. No. 7,527,942B2; US2009/0192101A1) or mixing specific promoters with sequence elements derived from strong constitutive promoters (Sakaguchi M. et al., Oncol. Rep. 2017 August; 38(2): 1108-1114). Both solutions can be considered a mixed success, since they increase promoter strength at the expense of leakiness and often result in a reduction in specificity.

A more recent strategy often labeled "miRNA detargeting" combines a constitutive promoter with targets for miRNA abundant in tissues to be excluded from the expression profile (WO2007/000668A2). This approach allows reaching high dosage of the transgene, due to the use of a constitutive promoter. While useful to refine targeting precision, reaching high-selectivity by detargeting alone in applications that rely on systemic delivery is difficult because it requires one-by-one exclusion of many tissues through a large set miRNA targets. As the number of targets increases, the cassette design becomes more challenging because of compositional effects and potential genetic instabilities (Ruiz A. J. et al., J. Virol. 2016 Mar. 28; 90(80): 4078-4092). Furthermore tight Off levels require the presence of highly abundant miRNA, potentially limiting the number of usable molecular targets.

A version of miRNA targeting—proposed earlier by Rinaudo et al. using a plasmid-encoded gene circuit (Rinaudo K. et al., Nature Biotechnol. 2007 July; 25(7): 795-801)—was attempted in lentiviral vectors (Amendola M. et al., Mol. Ther. 2013 May; 21(5): 934-946). Interestingly, the study implements the approach using two distinct lentiviral vectors, and thus, exemplifies that packaging complex gene circuits into a contiguous DNA molecule is a challenging task.

Synthetic Biology: A wide array of circuits exhibiting complex logic behavior have been described. The implementation of all possible one- and two-inputs logic gates in mammalian cells has been shown before using transcriptional and translational regulators (Auslander S. et al., Nature. 2012 Jul. 5; 487(7405): 123-27). More recently several groups demonstrated and described implementations of molecular logic and memory based on recombinases (WO2014/093852A1; WO2015/188191A1).

These efforts showcase outstanding progress in cell control and logic implementation using biomolecules. However all these systems suffer two shortcomings when it comes to their use for in vivo cell targeting: (i) interface matching and (ii) circuit size.

Previously described circuits were tested with well characterized and externally modulated ectopic input molecules in cell culture, and there is no proof of their performance when interfaced with endogenous cellular molecules. While great progress has been made in developing logic integration, the creation of logic circuit-cellular environment interfaces still lags behind. Examples of endogenous miRNA as effective logic inputs was shown before using sets of recombinant plasmids delivered to cultured cell lines (WO2012/012739A2). Logic gene circuits able to process endogenous transcription factor inputs were shown with two full-length tissue-specific promoters each controlling a fragment of a split proteins (Nissim L. and Bar-Ziv R. H., Mol. Syst. Biol. 2010 Dec. 21; 6:444) or Cas9 and a gRNA (Liu Y. C. et al., Nat. Commun. 2014 Nov. 6; 5: 5393). A system capable of robustly interfacing single endogenous transcription factors to synthetic circuits and pairs of unrelated transcription factors has also be demonstrated (Angelici B. et al., Cell Rep. 2016 Aug. 30; 16(9): 2525-2537). However, in all the above cases the experimental implementations—and in particular in Angelici B. et al. (Cell Rep. 2016 Aug. 30; 16(9): 2525-2537)—were limited to mixtures of recombinant plasmids transiently transfected to cultured cells. In no case was it shown that the logic circuits could be implemented in a contiguous nucleic acid molecule or in medically relevant vector systems or shown to treat disease in animal models.

In addition, most of the above mentioned designs aim at maximal flexibility of the circuit function, and this is usually achieved by constructing additional recombinant plasmids. Indeed, many complex circuits require 10 separate plasmids to operate in the transient transfection scenario. As an example, the 2-input AND gate described in Auslander et al. (Nature. 2012 Jul. 5; 487(7405): 123-27) requires 5 different plasmids and the recombinase system described by W. Wong (WO2015/188191A1) relies on 3 plasmids (two recombinases plus the output expression cassette they operate on), and neither has been tested in conjunction with endogenous cell inputs. Moreover, previously described systems designed to implement AND logic required 3 plasmids (Liu Y. C. et al., Nat. Commun. 2014 Nov. 6; 5: 5393; Angelici B. et al., Cell Rep. 2016 Aug. 30; 16(9): 2525-2537). These approaches also require the use of full mammalian promoters as interface with cellular background, and in one case use of a large protein (CAS9) for logic integration results in a very large circuit size.

Gene circuits for therapeutic applications: Implementation of multicomponent gene circuits in therapeutically relevant viral and non-viral vectors in still very rare, not the least due the above-mentioned fact that many state of the art circuits are increasingly complex and require a large DNA footprint. Additional challenges of integrating multiple genes on a contiguous DNA molecule discussed above (e.g., read-through, regulatory interference between genes, etc.) have prevented medical translation of many of the basic advances described above. Existing examples of logic circuit for in vivo targeting have been limited to lentiviral vectors (Morel M. et al., Proc. Natl. Acad. Sci. U.S.A. 2016 Jul. 19; 113(29): 8133-8138; Nissim L. et al., Cell. 2017 Nov. 16; 171(5): 1138-1150) due to their higher cargo capacity. While useful for ex-vivo applications (in particular immune cells engineering), lentiviral backbones are far from ideal for in vivo therapy due to their ability to integrate in the host genome causing mutations and/or unwanted gene activation. The gene circuit shown in Nissim L. et al. (Cell. 2017 Nov. 16; 171(5): 1138-1150) is implemented using a pair of lentiviral constructs, rather than a single vector, underlying the difficulty of encoding complex gene circuits in contiguous DNA molecules as shown herein. As shown in the Examples herein and in FIGS. 3A-3B, FIGS. 5A-5C, FIGS. 6A-6B, and FIGS. 7A-7B, a non-integrating single-component AAV vector represents a safe, proven alternative, with a wide selection of serotypes optimized for efficient delivery in different cell types and high ability to penetrate tumors but is limited in cargo capacity. The data in Morel et al. (Morel M. et al., Proc. Natl. Acad. Sci. U.S.A. 2016 Jul. 19; 113(29): 8133-8138) also show how the poor On: Off characteristic of natural specific promoter affect circuit performance, imposing a tight trade-off between sensitivity and specificity. The drawbacks of these tools notwithstanding, the specific methods used in Morel M. et al. (Proc. Natl. Acad. Sci. U.S.A. 2016 Jul. 19; 113(29): 8133-8138) and Nissim L. et al. (Cell. 2017 Nov. 16; 171(5): 1138-1150) are non-overlapping with the current disclosure.

EXAMPLES

Example 1. Functionalities Implemented in a Contiguous DNA Molecule

Figure 1A:
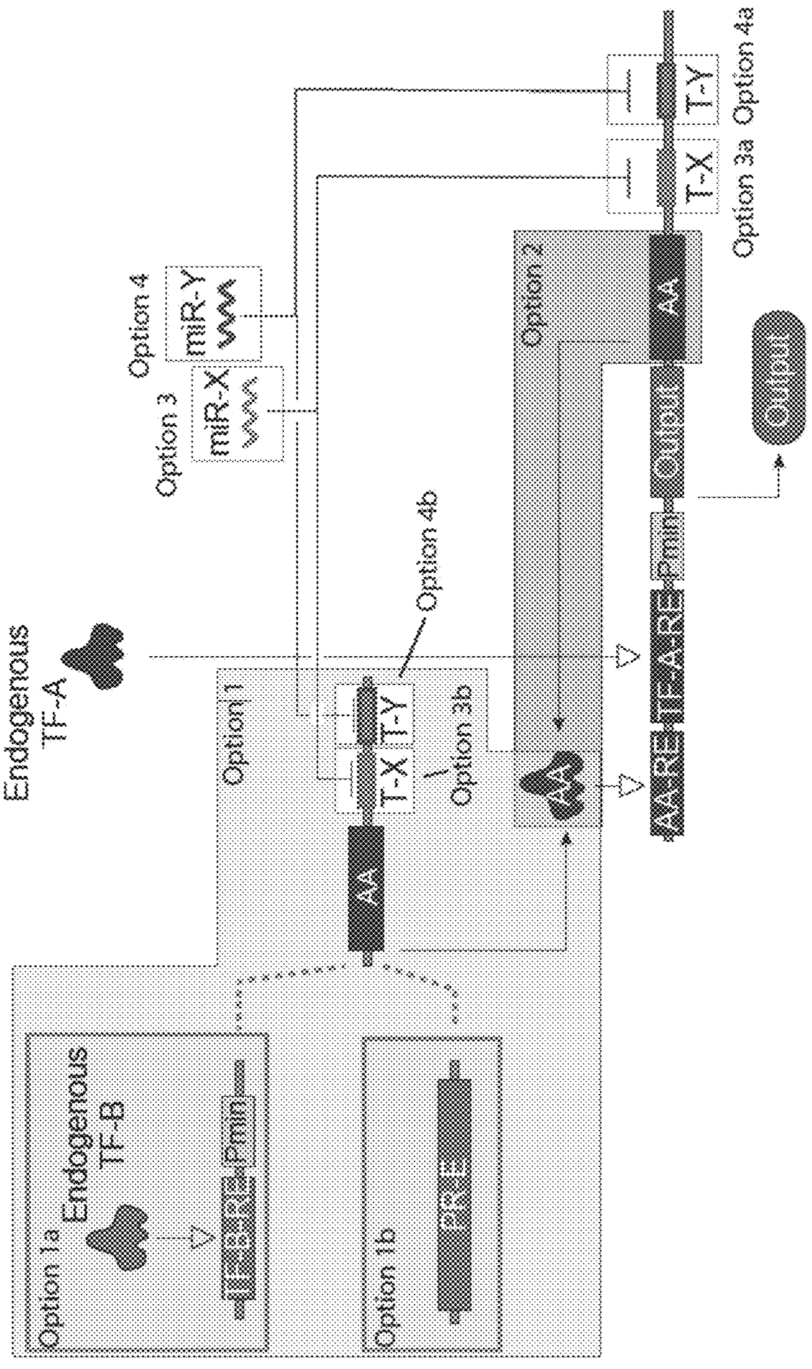

Described herein is a contiguous DNA construct capable of implementing multi-input logic, for example between two transcription factors (TFs), between an endogenous promoter (or promoter fragment) and an arbitrary transcription factor, and optionally one or more microRNA (miRNA). The inputs are typically chosen such that their combination is unique to one or more physiological cell states that the circuit is designed to target. A general circuit architecture schematic is shown in FIG. 1A. An arbitrary transcription factor A (TF-A) binds to a response element in the promoter region (TF-A-RE) of the output gene next to a minimal promoter (Pmin). Elsewhere in this promoter region there is a binding site for a protein termed an "auxiliary transactivator" (AA). AA is a transcriptional transactivator that is capable of activating gene expression when bound to its response element (AA-RE) and in the presence of a minimal promoter. The promoter region containing the response element for a transcription factor A and auxiliary transactivator AA has a synergistic behavior, namely, the expression of the output driven by either the transcription factor A or the auxiliary transactivator AA alone is less than the expression of the output in the presence of both the former and the latter (Angelici B. et al., Cell Rep. 2016 Aug. 30; 16(9): 2525-2537).

In "option 1a" of the circuit in FIG. 1A, the AA protein expression is driven by arbitrary transcription factor B that binds to a response element (TF-B-RE) in the promoter region of the AA-coding gene next to a minimal promoter. In this option, the output is strongly expressed when both TF-A and TF-B are strongly active, implementing an AND-like logic behavior between TF-A and TF-B, "TF-A AND TF-B" (TABLE 1). Alternatively the AA expression can be driven by the promoter of an endogenous gene (PR-E) or one or more fragment of such promoter ("option 1b" of the circuit in FIG. 1A). In this case the output is strongly expressed only when the endogenous promoter is active concurrently with a highly active TF-A, implementing the logic "PR-E AND TF-A" (TABLE 1).

TABLE 1

Output levels under the indicated conditions.

| TF-A/PR-E | TF-B | Output |
|---|---|---|
| High | High | 100% |
| High | Low | At most 50% |
| Low | High | At most 50% |
| Low | Low | At most 20% |

In "option 2" of the circuit in FIG. 1A, the AA protein expression is coupled to the output expression, e.g., via a T2A linker. In this option, the output is proportional to the strength of the TF-A (or alternatively and/or in addition to a PR-E) amplified by the AA action (Angelici B. et al., Cell Rep. 2016 Aug. 30; 16(9): 2525-2537).

TABLE 2

Output levels under the indicated conditions.

| TF-A | Output |
|---|---|
| High | 100% |
| Low | At most 50% |

In "option 3" of the circuit in FIG. 1A, the output is further controlled by an arbitrary microRNA (miR-X) via target sites in the mRNA encoding the output. In "option 3a" only the output gene is controlled by the miRNA while in "option 3b" (only compatible with the option 1 above) the gene encoding the AA is controlled by the same miRNA. "Options 3a" and "option 3b" can be used together or separately.

"Option 1a" in combination with "option 3a," "option 3b," or both, results in a logic behavior of "TF-A AND TF-B and NOT(miR-X)," namely, the output will be highly expressed upon concurrent presence of TF-A and TF-B and in the absence of miR-X (TABLE 2). Similarly "option 1b" can be combined with "option 3a," "option 3b," or both to implement logic behavior of the type "PR-E AND TF-A AND NOT (miR-X)" (TABLE 2).

TABLE 3

Output levels under the indicated conditions.

| TF-A/PR-E | TF-B | microRNA-X | Output |
|---|---|---|---|
| High | High | Low | 100% |
| High | Low | Low | At most 50% |
| Low | High | Low | At most 50% |
| Low | Low | Low | At most 20% |
| High | High | High | At most 20% |
| High | Low | High | At most 20% |
| Low | High | High | At most 20% |
| Low | Low | High | At most 20% |

"Option 2" in combination with "option 3a" results in a logic behavior of "TF-B AND NOT(miR-X)," namely, the output will be highly expressed in the presence of TF-B and in the absence of miR-X.

TABLE 4

Output levels under the indicated conditions.

| TF-A | microRNA-X | Output |
|---|---|---|
| High | Low | 100% |
| Low | Low | At most 50% |
| High | High | At most 50% |
| Low | High | At most 20% |

In "option 4" of the circuit in FIG. 1A, the output is further controlled by an arbitrary microRNA (miR-Y) via target sites in the mRNA encoding the output. In "option 4a" only the output gene is controlled by the miRNA while in "option 4b" (only compatible with the "option 1" above) the gene encoding the AA is controlled by the same miRNA. "Option 4a" and "option 4b" can be used together or separately.

"Option 1a" in combination with "option 3a," "option 3b," or both, and "option 4a," "option 4b," or both results in a logic behavior of "TF-A AND TF-B AND NOT(miR-X) AND NOT(miR-Y)," namely, the output will be highly expressed upon concurrent presence of TF-A and TF-B and in the absence of miR-X and miR-Y. The utility of this arrangement is to prevent output expression in the tissues that strongly express miR-X or miR-Y or both, thus improving safety features, while retaining strong expression in cells that express both TF-A and TF-B but none of the miR-X and miR-Y. Likewise "option 1b" can be combined with "option 3a," "option 3b," or both, and "option 4a," "option 4b," or both to implement the logic "PR-E AND TF-B AND NOT (miR-X) AND NOT(miR-Y)."

"Option 2" in combination with "option 3a" and "option 4a" results in a logic behavior of "TF-A AND NOT(miR-X) AND NOT(miR-Y)," namely, the output will be highly expressed in the presence of TF-B and in the absence of miR-X and in the absence of miR-Y.

Additional miRNA inputs and their binding sites can be added and the circuit structure and logic behavior can be expanded in an analogous fashion (e.g., miR-Z as another input feature, and structural "option 5a" and "option 5b," etc.). Specific genetic implementations of these regulatory programs are exemplified by the structures in FIG. 2.

Example 2. Implementation in a Contiguous DNA Cassette and Integration with Viral Vectors As described herein, representative examples of the circuits described in Example 1 were implemented in contiguous DNA molecules and further incorporated into viral vector genomes, upon which viral particles were produced and tested for their ability to selectively target cells in vitro and in vivo, and curb tumor growth in vivo. Therefore, among other things, a specific example of a therapeutic utility of this approach is disclosed. The genes are integrated in a contiguous DNA construct in either a convergent or divergent orientation. In the latter, response elements for the transcription factor inputs are located in the center of the DNA molecule (between the two coding sequences), and miRNA targets and PolyA are adjacent to the viral backbone of choice (FIG. 2). One may also integrate the genes in a head-to-tail (co-linear) fashion; this has not been tried experimentally as similar systems were problematic in the past, but it is also possible that head-to-tail orientation would be functional. Further, insulators can be placed between the individual genetic modules to improve their isolation from each other and from the viral vector context. Lastly, the approach can lead to conditionally-replicating ("oncolytic") vectors where the output gene is a gene or genes naturally responsible for a vector replication (FIG. 2).

Example 3. Preferred Embodiments and Functional Demonstration

One preferred embodiment is a divergent head-to-head arrangement. In this configuration, the components' physical organization maximizes functionality and minimizes unpredictable context effects, resulting in a robust modular system. Divergent genes avoid the risk of transcriptional run-through. Transcriptional regulation is directed toward response elements located in the center of the construct, surrounded by genetic components that remain relatively constant (the minimal promoter is usually unchanged, while transactivator and output genes are selected from a list of well characterized components). Therefore, the intended transcriptional regulation is sheltered from cryptic regulators or TF binding sites present on the viral backbone. The miRNA targets act through post-transcriptional regulation, and therefore they are unaffected by spurious binding of e.g. transcription factors to adjacent viral sequences. Superior performance of the embodiment with divergent configuration in shown in FIGS. 3A-3B, where there is a clear gain in gene expression when "option 1" is used in combination with "option 3a" or "option 3b." This experiment was done using naked DNA prior to viral packaging; thus, in subsequent viral vector embodiments only the divergent configuration was employed.

Figure 4A:
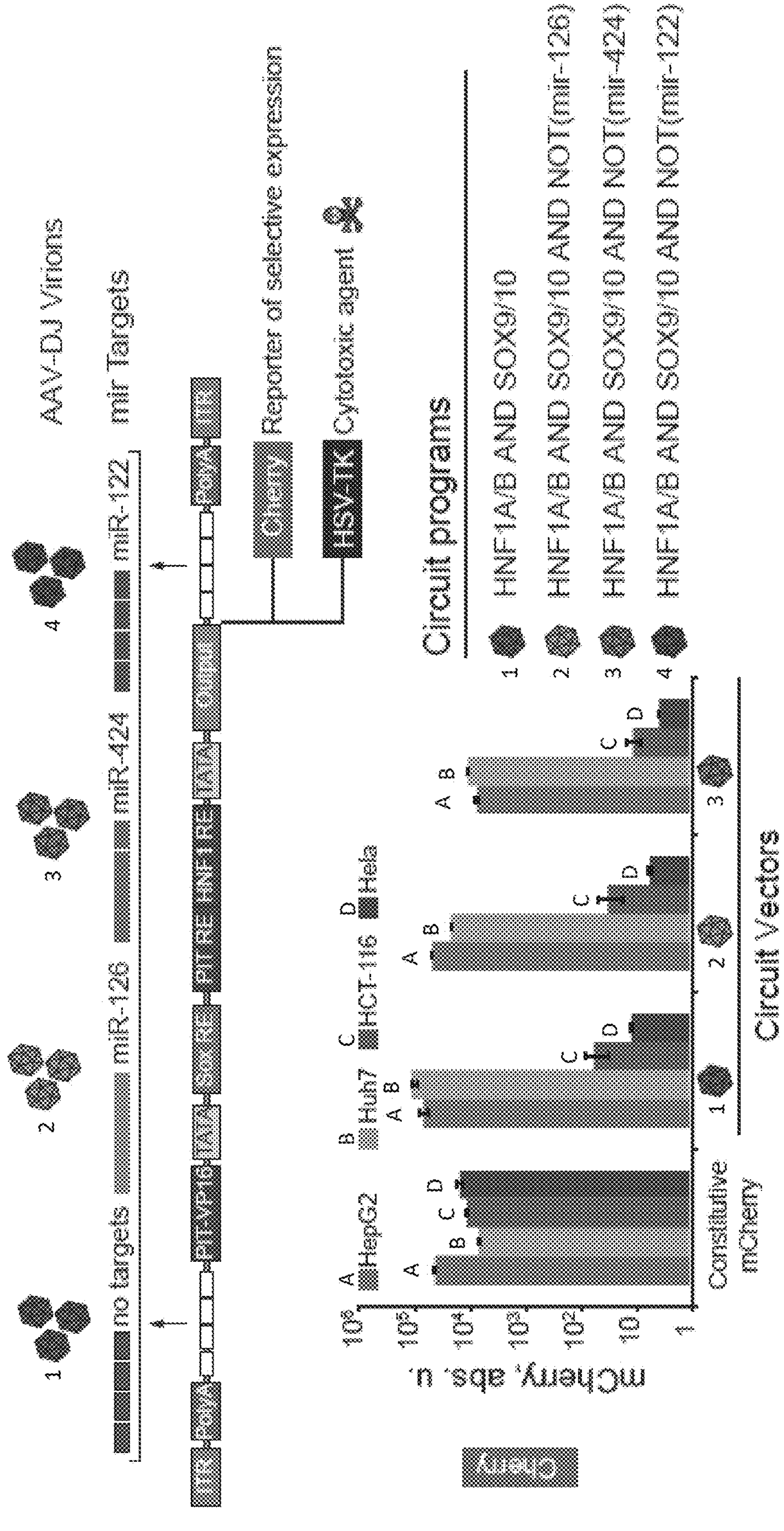
FIGS. 4A-4B. Demonstration of AAV virions implementing gene circuits in accordance with the current disclosure.
Figure 4B:
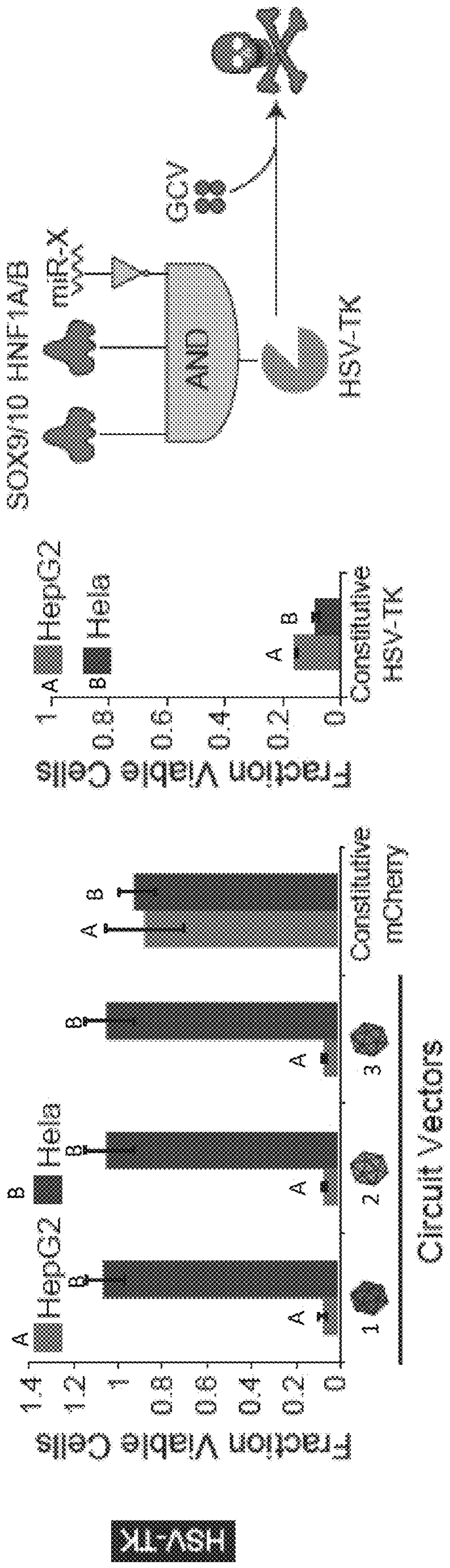

The function of the contiguous DNA cassette was demonstrated in an adeno-associated viral vector (AAV) and in a lentiviral vector. In FIGS. 4A-4B, the in vitro function of a number of AAV vectors implementing divergent configuration and circuit architecture combining "option 1" with "options 3a" and "option 3b" are shown (FIG. 1A). The DNA was packaged into AAV-DJ types virions (Grimm D.

et al., J. Virol., 2008 June; 82(12): 5887-5911). Each vector was generated in two variants: (i) a fluorescent output mCherry to test targeting specificity and (ii) a cytotoxic output HSV-TK to test for selective anti-tumor activity. In FIG. 4A, the various vectors with fluorescent outputs were tested in a panel of cell lines. The circuit was programmed to detect a combination of Sox9/10 and HNF1A/B expression, typical of liver cancer (Zhou D. et al., Tumour Biol. 2014 October; 35(10):9935-40; Guo X. et al., Diagn. Pathol. 2012 Apr. 19; 7:44.). In addition, miRNA control elements were added to create a safety switch in healthy liver, based on the fact that these miRNA are highly expressed in mouse liver but not in liver cancer cells (internal profiling data). Liver cancer cell lines HepG2 and Huh7 were used as a positive control while two other non-liver cancer cell lines HeLa and HCT-116 were used as a negative control. As the bar chart in FIG. 4A shows, the fluorescent output is expressed at high levels in two liver cancer cell lines but not in the negative control cell lines. In FIG. 4B, cytotoxic activity is shown when the fluorescent output is replaced with HSV-TK gene and in combination with prodrug ganciclovir (GCV). HSV-TK (thymidine kinase) converts GCV to a cytotoxic product leading to cell death. Here as expected, the liver cancer cell line HepG2 is targeted by the vector, resulting in greatly reduced viability. The control cell line HeLa remains viable. The chart on the right shows that both cell lines are susceptible to HSV-TK+GCV action when HSV-TK is driven by a constitutive promoter and expressed at similar levels in both cell lines.

Figure 5A:
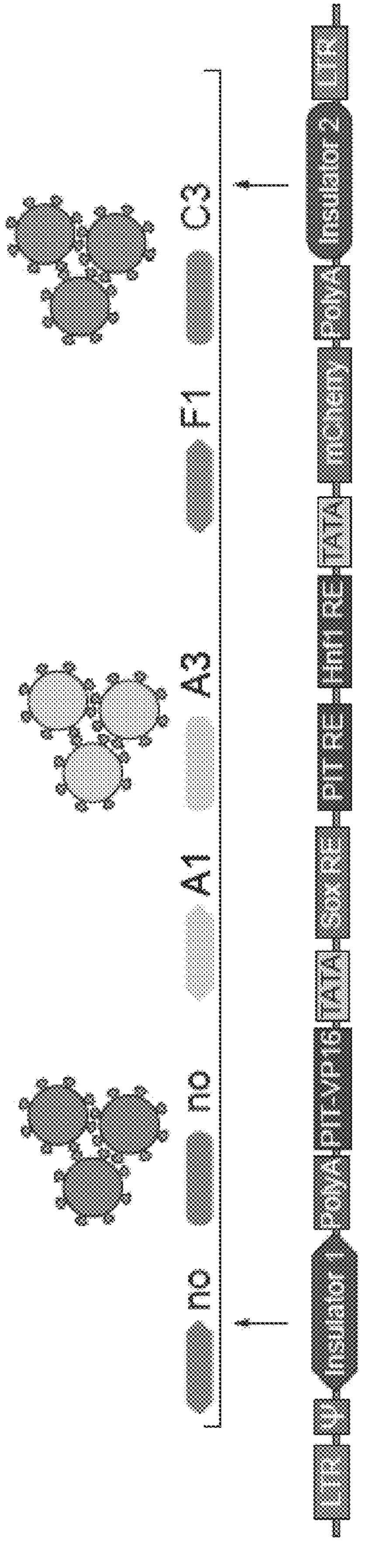
FIGS. 5A-5C. Implementation of one of the embodiments in a lentiviral vector.
Figure 5B:
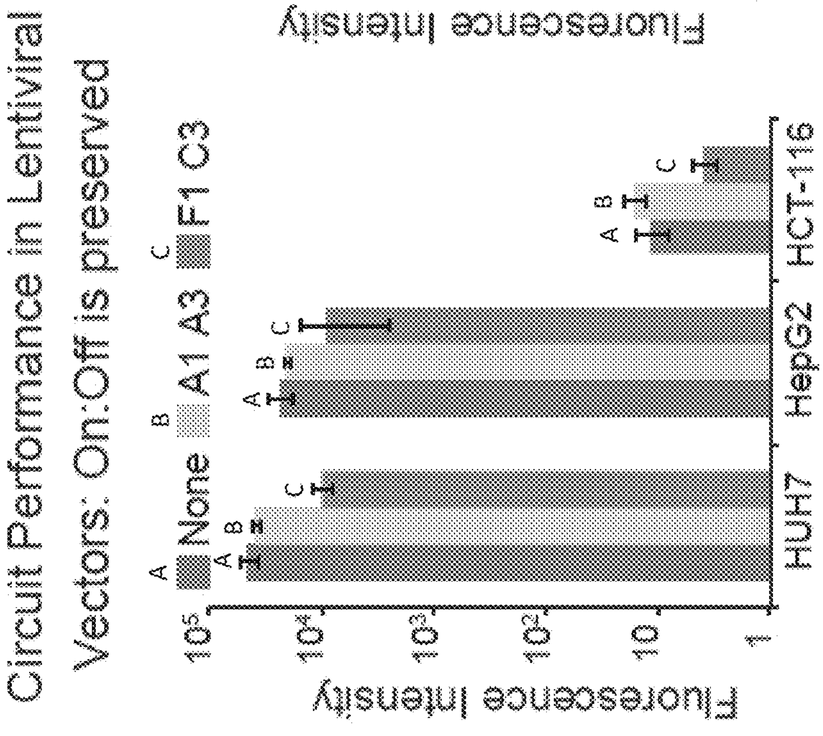
Figure 5C:
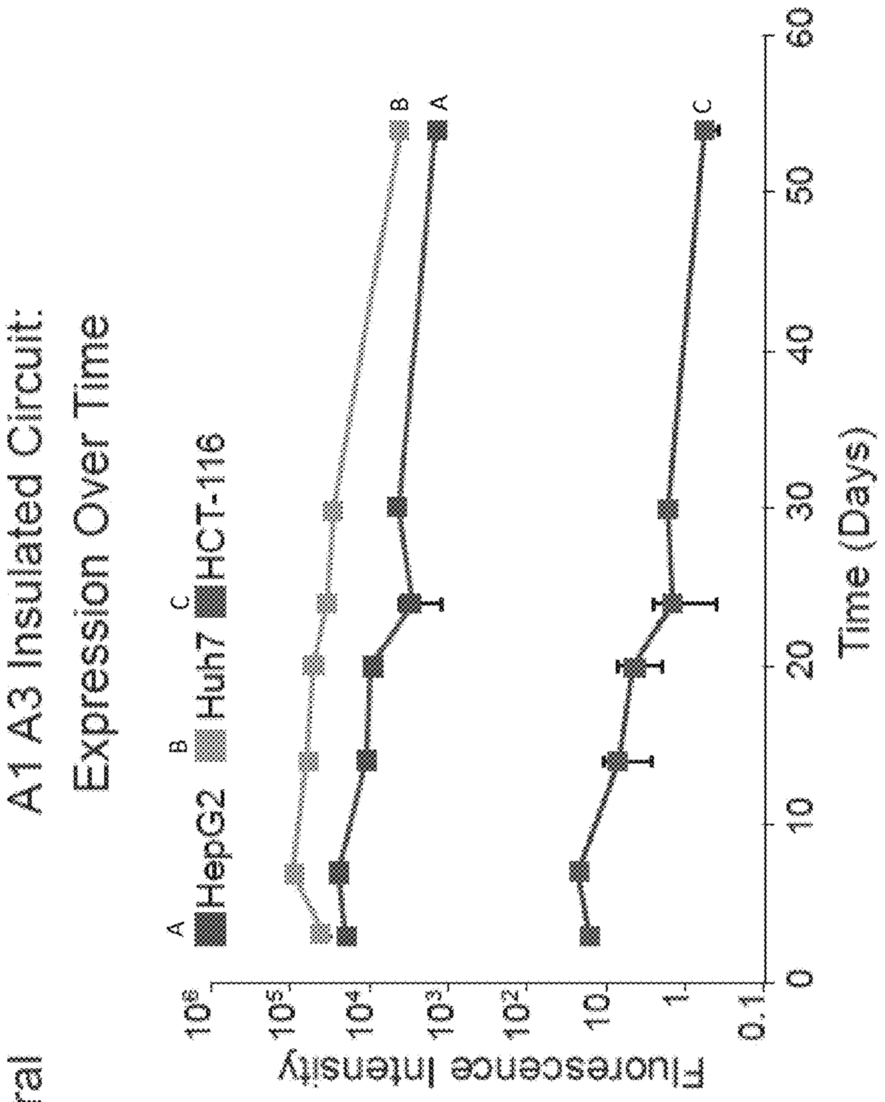

An additional divergent cassette implementing circuit "option 1" (FIG. 5A) was embedded in a lentiviral vector and tested for selective output expression in vitro with fluorescent output. Here, insulators were used to flank the cassette and two different insulator pairs were employed next to a construct without the insulator pair. All constructs showed comparable output expression in the positive control cell lines Huh7 and HepG2, and very low expression in the negative control cell line HCT-116 (FIG. 5B). These integrating vectors were also followed over time for up to 2 months, with only marginal loss in gene expression. In parallel, the negative control cell line showed consistent low expression (FIG. 5C).

Figure 6A:
FIGS. 6A-6B. Demonstration of specific cell targeting in vivo by the virions carrying contiguous DNA cassettes.
Figure 6B:
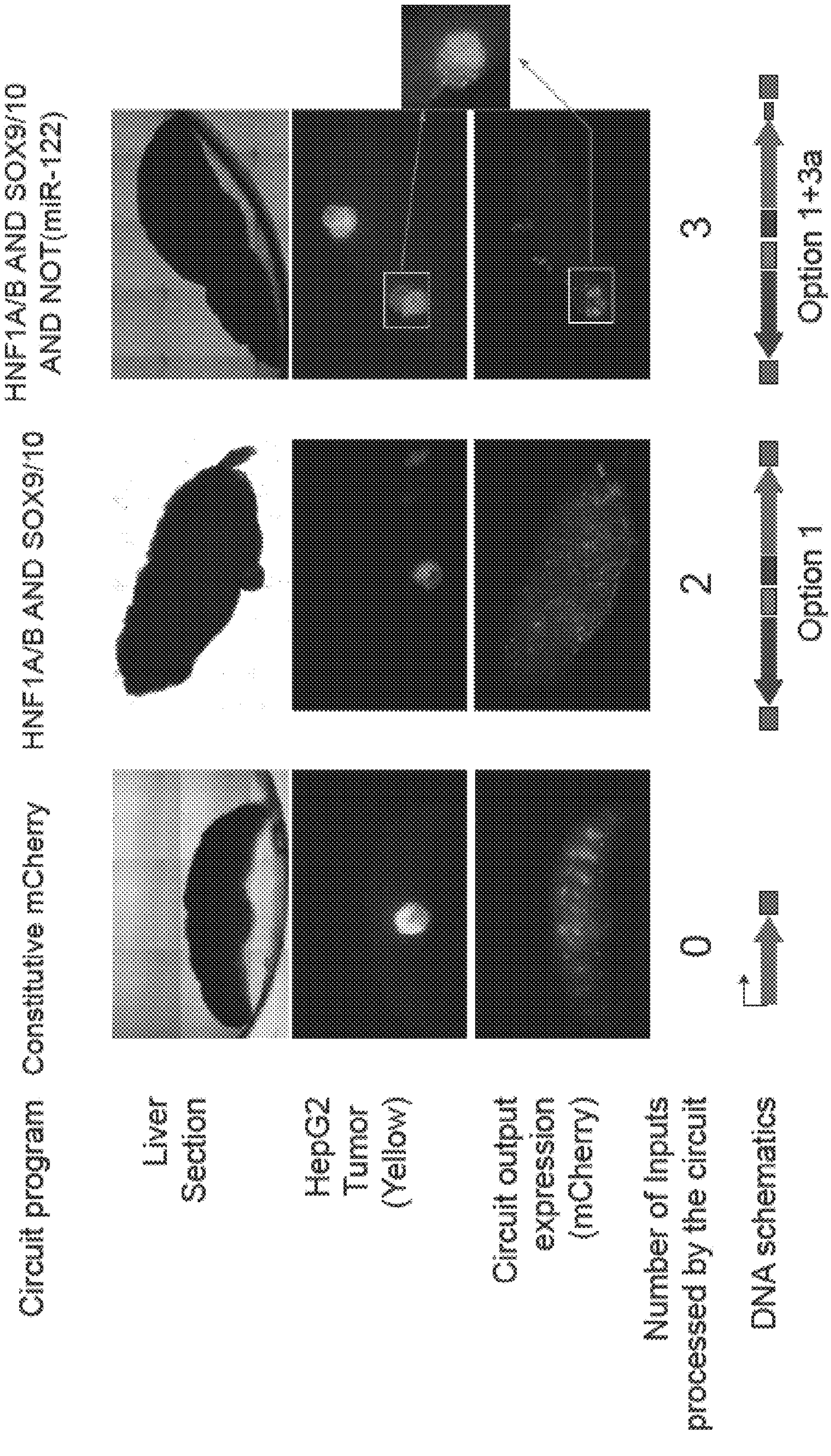

An AAV viral vector implementing a divergent DNA cassette and a circuit according to "option 1" with "option 3a," executing a cell targeting program "Sox9/10 AND HNF1A/B and NOT(miR-122)" was further tested in vivo in an orthotopic mouse model of disseminated liver cancer. Nod-SCID-Gamma (NSG) immunodeficient mice underwent surgery, in which HepG2 cancer cells were injected into the spleen, disseminated to the liver via portal circulation, and formed multiple tumor foci (FIG. 6A). The spleen was surgically excised to prevent primary tumor formation in the spleen. The cells had been previously augmented with YFP fluorescent reporter and Luciferase gene to enable in vivo tracking of tumor load and post-mortem examination of tumor foci. Following tumor cell injection and tumor establishment, AAV-DJ virions were injected systemically into the tail vein. In the first experiment (FIG. 6B) fluorescent reporter protein mCherry was used to gauge tumor-specific expression of the output. A variant of the circuit without the T-miR-122 feature ("option 1" only) was also tested as a reference, as well as a control vector expressing mCherry under a constitutive promoter. As the data in FIG. 6B show, the virion encoding the circuit that processes all three inputs is able to target the output gene expression to the tumor, while the circuit implementing "option 1" only results in bystander output expression in healthy liver.

Figure 7A:
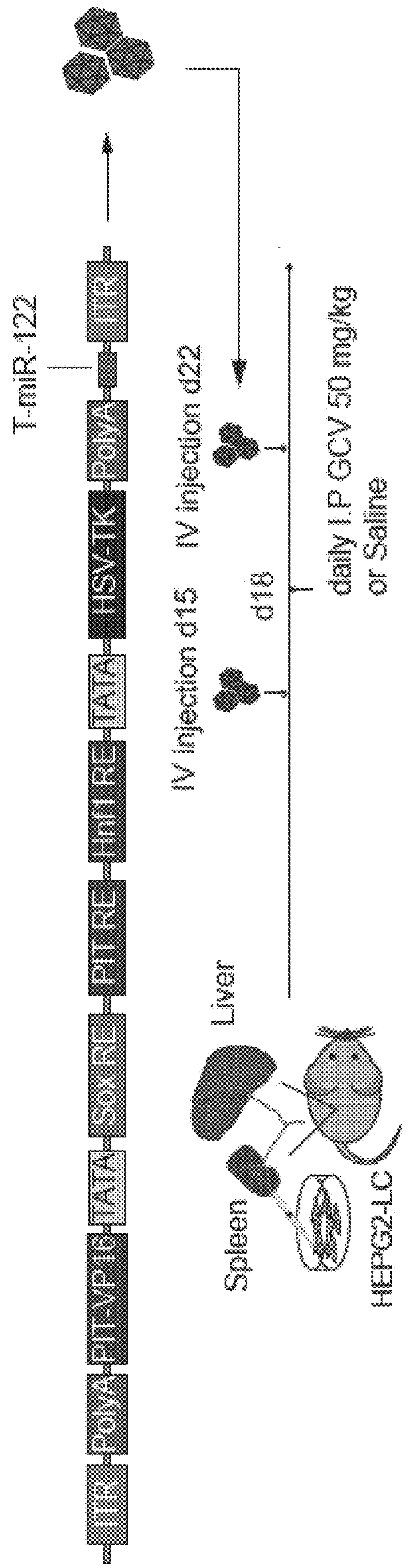
FIGS. 7A-7C. Demonstration of antitumor efficacy of a gene circuit-bearing viral vector.
Figure 7B:
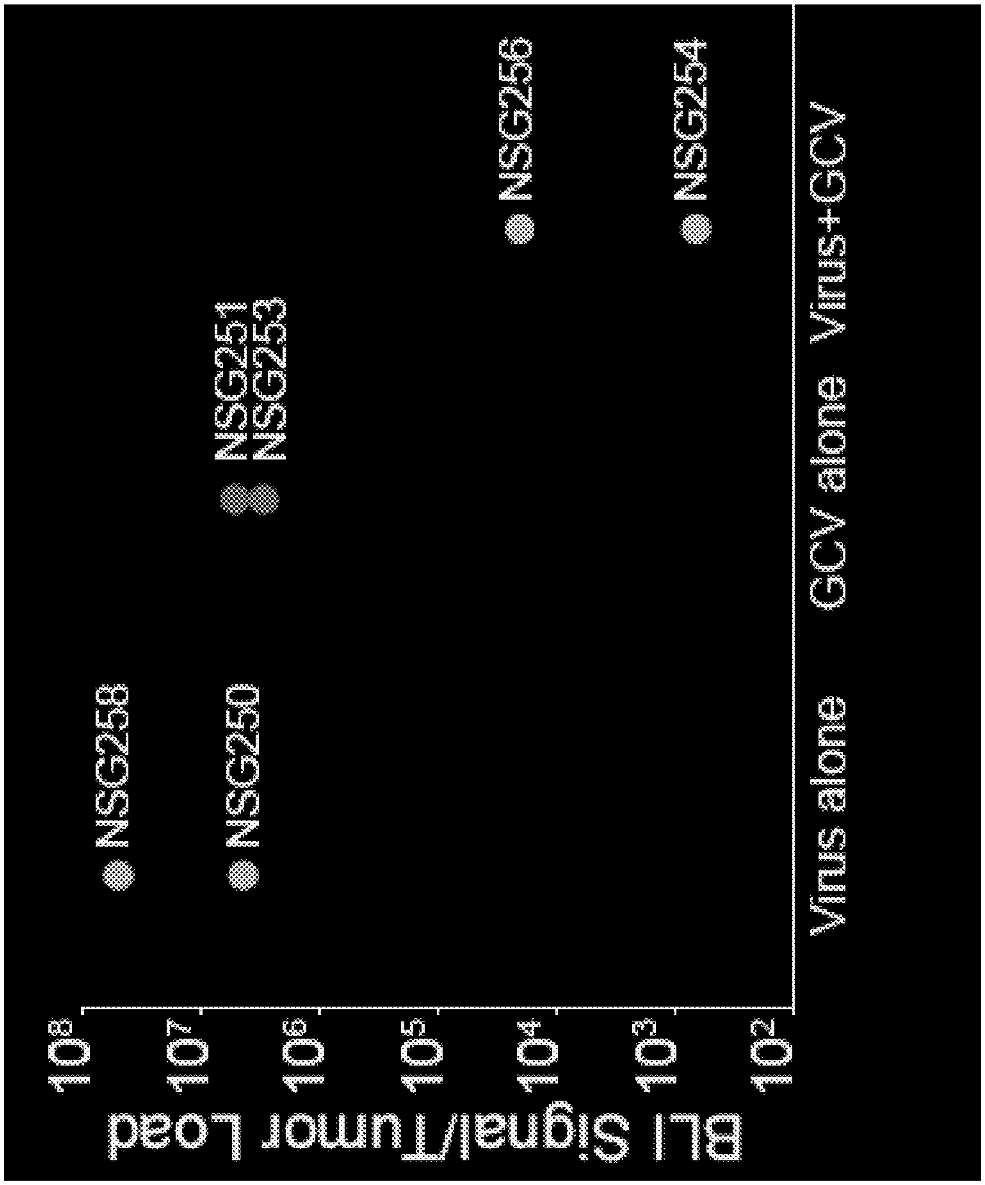
Figure 7C:
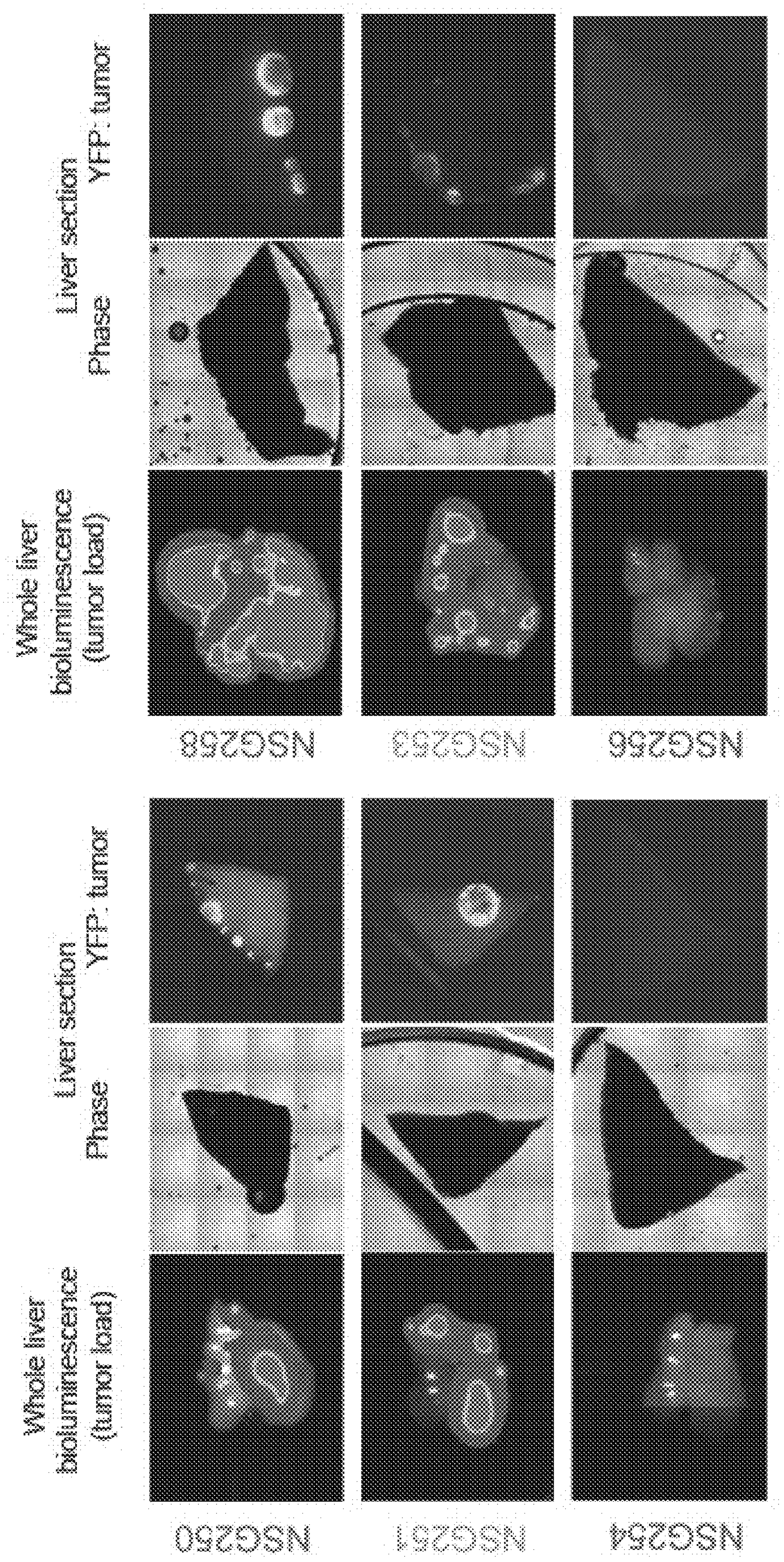

The vector implementing the three-input cell-targeting program was constructed with a cytotoxic output HSV-TK, which leads to cell death in the presence of small molecule prodrug ganciclovir (GCV) (FIG. 7A). The data show that the treated animals (viral vector injected twice in the tail vein followed by daily administration of ganciclovir) had much lower tumor load compared to the control groups (FIGS. 7B-7C). Thus, the antitumor potential was demonstrated of the virions that package contiguous DNA cassettes implementing multi-input classifier circuits.

REFERENCES

1. Xie Z., Wroblewska L., Prochazka L., Weiss R., and Beneson Y., Multi-input RNAi-based logic circuit for identification of specific cancer cells. Science. 2011 Sep. 2; 333(6047): 1307-11.
2. Benenson Y., Biomolecular computing systems: principles, progress and potential. Nat. Rev. Genet. 2012 Jun. 12; 13(7): 455-468.
3. Dorer D. E. and Nettelbeck D. M., Targeting cancer by transcriptional control in cancer gene therapy and viral oncolysis. Adv. Drug Deliv. Rev. 2009. 61(7-8): 554-571.
4. Robson T. and Hirst D. G., Transcriptional Targeting in Cancer Gene Therapy. J. Biomed. Biotechnol. 2003; 2003(2): 110-137.
5. Navarro S. A., Carrillo E., Grinan-Lison C., Martin A, Peran M, Marchal J. A., and Boulaiz H., Cancer suicide gene therapy: a patent review. Expert Opin. Ther. Pat. 2016 September; 26(9): 1095-1104.
6. Kanegae Y., Terashima M., Kondo S., Fukuda H., Maekawa A., Pei Z., and Saito I., High-level expression by tissue/cancer-specific promoter with strict specificity using a single-adenoviral vector. Nucleic Acids Res. 2011 January; 39(2): e7.
7. Iyer M., Wu L., Carey M., Wang Y., Smallwood A., and Gambhi S. S., Two-step transcriptional amplification as a method for imaging reporter gene expression using weak promoters. Proc. Natl. Acad. Sci. U.S.A. 2001 Dec. 4; 98(25): 14595-14600.
8. U.S. Pat. No. 7,527,942B2
9. US20090192101A1
10. Sakaguchi M., Sadahira T, Ueki H., Kinoshita R., Murata H., Yamamoto K. I., Futami J., Nasu Y., Ochiai K., Kumon H., Huh N. H., and Watanabe M., Robust cancer-specific gene expression by a novel cassette with hTERT and CMV promoter elements. Oncol. Rep. 2017 August; 38(2): 1108-1114.
11. WO2007/000668A2
12. Ruiz A. J., Hadac E. M., Nace R. A., and Russell S. J., MicroRNA-Detargeted Mengovirus for Oncolytic Virotherapy. J. Virol. 2016 Mar. 28; 90(80): 4078-4092.
13. Rinaudo K., Bleris L., Maddamsetti R., Subramanian S., Weiss R., and Benenson Y., A universal RNAi-based logic evaluator that operates in mammalian cells. Nature Biotechnol. 2007 July; 25(7): 795-801.
14. Amendola M., Giustacchini A., Gentner B., and Naldini L., A Double-Switch Vector System Positively Regulates Transgene Expression by Endogenous microRNA Expression (miR-ON Vector). Mol. Ther. 2013 May; 21(5): 934-946.
15. Auslander S., Auslander D., Muller M., Wieland M., and Fussenegger M., Programmable single-cell mammalian biocomputers. Nature. 2012 Jul. 5; 487(7405): 123-27.
16. WO2014/093852A1
17. WO2015/188191A1
18. WO2012/012739A2

19. Nissim L. and Bar-Ziv R. H., A tunable dual-promoter integrator for targeting of cancer cells. Mol. Syst. Biol. 2010 Dec. 21; 6:444.
20. Liu Y. C., Zeng Y., Liu L., Zhuang C., Fu X., Huang W., and Cai Z., Synthesizing AND gate genetic circuits based on CRISPR-Cas9 for identification of bladder cancer cells. Nat. Commun. 2014 Nov. 6; 5: 5393.
21. Angelici B., Mailand E., Haefliger B., and Benenson Y., Synthetic Biology Platform for Sensing and Integrating Endogenous Transcriptional Inputs in Mammalian Cells. Cell Rep. 2016 Aug. 30; 16(9): 2525-2537 (2016).
22. Morel M., Shtrahman R., Rotter V., Nissim L. and Bar-Ziv R. H., Cellular heterogeneity mediates inherent sensitivity-specificity tradeoff in cancer targeting by synthetic circuits. Proc. Natl. Acad. Sci. U.S.A. 2016 Jul. 19; 113(29): 8133-8138.
23. Nissim L., Wu M. R., Pery E., Binder-Nissim A., Suzuki H. I., Stupp D., Wehrspaun C., Tabach Y., Sharp P. A., and Lu T. K., Synthetic RNA-Based Immunomodulatory Gene Circuits for Cancer Immunotherapy. Cell. 2017 Nov. 16; 171(5): 1138-1150.
24. Zhou D., Bai F., Zhang X., Hu M., Zhao G., Zhao Z., and Liu R. SOX10 is a novel oncogene in hepatocellular carcinoma through Wnt/β-catenin/TCF4 cascade. Tumour Biol. 2014 October; 35(10):9935-40.
25. Guo X., Xiong L., Sun L., Peng R., Zou L., Zhu H., Zhang J., Li H. and Zhao J., Expression features of SOX9 associate with tumor progression and poor prognosis of hepatocellular carcinoma. Diagn. Pathol. 2012 Apr. 19; 7:44.
26. Grimm D., Lee J. S., Wang L., Desai T., Akache B., Storm T. A., and Kay M. A., In vitro and in vivo gene therapy vector evolution via multispecies interbreeding and retargeting of adeno-associated viruses. J. Virol., 2008 June; 82(12): 5887-5911.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B," when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B," the disclosure also contemplates the alternative embodiments "a composition consisting of A and B" and "a composition consisting essentially of A and B."

What is claimed is:

1. A contiguous polynucleic acid molecule encoding a classifier gene circuit comprising at least two cassettes, wherein each cassette comprises a regulatory component and a response component, wherein:

(i) at least one cassette comprises: a 5' regulatory component comprising a transactivator response element, a transcription factor response element and a minimal promoter, and a 3' response component comprising a sequence encoding an output; and (ii) at least one cassette comprises: a 5' regulatory component and a 3' response component comprising a nucleic acid sequence encoding a transactivator protein, wherein the transactivator of (ii), when expressed as a protein, binds and transactivates the transactivator response element of (i), and wherein the 5' regulatory component of cassette (ii) comprises a transcription factor response element, wherein the expression of the output driven by either a transcription factor binding to the transcription factor response element of cassette (i) alone, or by the transactivator protein bound to the transactivator response element of cassette (i) alone, is less than the expression of the output in the presence of both said transcription factor and said transactivator protein, wherein the at least one cassette of (i) and the at least one cassette of (ii) are in a divergent orientation, wherein the 3' response component of the at least one cassette of (i) and/or the at least one cassette of (ii) comprises at least one microRNA target site, and wherein the transcription factor response elements in (i) and (ii), and the microRNA target site, are sensors of inputs of the classifier gene circuit that controls the expression of the output.

2. The contiguous polynucleic acid molecule of claim 1, wherein the transactivator of cassette (ii) binds and transactivates the transactivator response element only in the presence of a transcription factor bound to the transcription factor response element of cassette (i).

3. The contiguous polynucleic acid molecule of claim 1, wherein the 5' regulatory component in (i) comprises from 5' to 3': the transactivator response element, the transcription factor response element, and the minimal promoter; or wherein the 5' regulatory component in (i) comprises from 5' to 3': the transcription factor response element, the transactivator response element, and the minimal promoter; or wherein the 5' regulatory component in (i) further comprises a promoter element, optionally wherein the promoter element comprises a mammalian promoter or promoter fragment or wherein the 5' regulatory component in (i) comprises from 5' to 3': a transactivator response component and a promoter element and, a minimal promoter.

4. The contiguous polynucleic acid molecule of claim 1, wherein the 3' response component of the cassette in (i) comprises the at least one microRNA target site.

5. The contiguous polynucleic acid molecule of claim 4, wherein the at least one microRNA target site is 3' to the sequence encoding the output.

6. The contiguous polynucleic acid molecule of claim 1, wherein the output is a protein or an RNA molecule; or wherein the output comprises a therapeutic;

optionally wherein the output comprises a fluorescent protein, a cytotoxin, an enzyme catalyzing a prodrug activation, an immunomodulatory protein and/or RNA, a DNA-modifying factor, cell-surface receptor, a gene expression-regulating factor, a kinase, an epigenetic modifier, and/or a factor necessary for vector replication;

further optionally wherein the immunomodulatory protein and/or RNA comprises a cytokine or a colony stimulating factor; or wherein the DNA-modifying factor comprises a gene encoding a protein intended to correct a genetic defect, a DNA-modifying enzyme, and/or a component of a DNA-modifying system, preferably wherein the DNA-modifying enzyme is a site-specific recombinase, homing endonuclease, or a protein component of a CRISPR/Cas DNA modification system; or wherein the gene expression-regulating factor comprises a protein capable of regulating gene expression or a component of a multi-component system capable of regulating gene expression.

7. The contiguous polynucleic acid molecule of claim 1, wherein the 5' regulatory component of cassette (ii) comprises a minimal promoter.

8. The contiguous polynucleic acid molecule of claim 1, wherein the 5' regulatory component of cassette (ii) comprises a mammalian promoter or promoter fragment.

9. The contiguous polynucleic acid molecule of claim 1, wherein the 3' response component of cassette in (ii) comprises the at least one microRNA target site.

10. The contiguous polynucleic acid molecule of claim 9, wherein the at least one microRNA target site is 3' to the nucleic acid sequence encoding the transactivator protein.

11. The contiguous polynucleic acid molecule of claim 1, wherein at least one of the cassettes is flanked by an insulator.

12. The contiguous polynucleic acid molecule of claim 1, wherein the transactivator protein is NarLc-VP16 or NarLc-RelA.

13. The contiguous polynucleic acid molecule of claim 1, wherein the classifier gene circuit results in differential expression of the output in a target cell compared to a non-target cell, wherein the target cell and the non-target cell differ in protein level or activity of an endogenous transcription factor that binds the transcription factor response element of cassette (i) or cassette (ii).

14. A vector or an engineered viral genome comprising the contiguous polynucleic acid molecule of claim 1.

15. The engineered viral genome of claim 14, wherein the viral genome is an adeno-associated virus (AAV) genome, a lentivirus genome, an adenovirus genome, a herpes simplex virus (HSV) genome, a Vaccinia virus genome, a poxvirus genome, a Newcastle Disease virus (NDV) genome, a Coxsackievirus genome, a rheovirus genome, a measles virus genome, a Vesicular Stomatitis virus (VSV) genome, a Parvovirus genome, a Seneca valley viral genome, a Maraba virus genome or a common cold virus genome.

16. A virion comprising the engineered viral genome of claim 14.

* * * * *